United States Patent
Stinson et al.

(10) Patent No.: US 8,523,907 B2
(45) Date of Patent: Sep. 3, 2013

(54) PROSTHESES, TOOLS AND METHODS FOR REPLACEMENT OF NATURAL FACET JOINTS WITH ARTIFICIAL FACET JOINT SURFACES

(75) Inventors: David Stinson, Woodinville, WA (US); Lawrence R. Jones, Conifer, CO (US); Robert M. Scribner, Niwot, CO (US); Mark A. Reiley, Piedmont, CA (US)

(73) Assignee: GMEDelaware 2 LLC, Audubon, PA (US)

( * ) Notice: Subject to any disclaimer, the term of this patent is extended or adjusted under 35 U.S.C. 154(b) by 1682 days.

(21) Appl. No.: 11/275,447

(22) Filed: Jan. 3, 2006

(65) Prior Publication Data

US 2006/0100707 A1 May 11, 2006

Related U.S. Application Data

(63) Continuation of application No. 10/615,417, filed on Jul. 8, 2003, now Pat. No. 7,074,238.

(51) Int. Cl.
*A61B 17/70* (2006.01)

(52) U.S. Cl.
USPC .......................................... 606/247; 606/277

(58) Field of Classification Search
USPC .................. 606/60, 246–250, 257, 276, 277, 606/330; 623/17.11–17.16
See application file for complete search history.

(56) References Cited

U.S. PATENT DOCUMENTS

| | | | |
|---|---|---|---|
| 1,308,451 A | 7/1919 | Schachat | |
| 2,502,902 A | 4/1950 | Tofflemire | |
| 2,930,133 A | 3/1960 | Thompson | |
| 2,959,861 A | 11/1960 | Stromquist | |
| 3,596,656 A | 8/1971 | Kaute | |
| 3,710,789 A | 1/1973 | Ersek | |
| 3,726,279 A | 4/1973 | Barefoot et al. | |
| 3,867,728 A | 2/1975 | Stubstad et al. | |
| 3,875,595 A | 4/1975 | Froning | |
| 3,941,127 A | 3/1976 | Froning | |
| 4,040,130 A | 8/1977 | Laure | |
| 4,123,848 A | 11/1978 | Emmerich et al. | |
| 4,156,296 A | 5/1979 | Johnson et al. | |
| 4,210,317 A | 7/1980 | Spann et al. | |
| 4,231,121 A | 11/1980 | Lewis | |

(Continued)

FOREIGN PATENT DOCUMENTS

| | | |
|---|---|---|
| DE | 10135771 A1 | 7/2001 |
| DE | 10312755 A1 | 10/2003 |

(Continued)

OTHER PUBLICATIONS

Abraham, D.J. et al. Indications and Trends in Use in Cervical Spinal Fusions. *Orthop Clin North Am.* Oct. 1998; 29(4):731-44.

(Continued)

*Primary Examiner* — Kevin T Truong
*Assistant Examiner* — Michael Araj

(57) ABSTRACT

Cephalad and caudal vertebral facet joint prostheses and methods of use are provided. The cephalad prostheses are adapted and configured to be attached to a lamina portion of a vertebra without blocking a pedicle portion of the cephalad vertebra. In some embodiments, the prosthesis is attached with a non-invasive support member, such as a clamp. In other embodiments, a translaminar screw may be used for additional fixation.

20 Claims, 12 Drawing Sheets

(56) References Cited

U.S. PATENT DOCUMENTS

| | | |
|---|---|---|
| 4,271,836 A | 6/1981 | Bacal et al. |
| 4,349,921 A | 9/1982 | Kuntz |
| 4,394,370 A | 7/1983 | Jefferies |
| 4,472,840 A | 9/1984 | Jefferies |
| 4,502,161 A | 3/1985 | Wall |
| 4,554,914 A | 11/1985 | Kapp et al. |
| 4,611,581 A | 9/1986 | Steffee |
| 4,633,722 A | 1/1987 | Beardmore et al. |
| 4,693,722 A | 9/1987 | Wall |
| 4,697,582 A | 10/1987 | William |
| 4,710,075 A | 12/1987 | Davison |
| 4,759,769 A | 7/1988 | Hedman et al. |
| 4,772,287 A | 9/1988 | Ray et al. |
| 4,778,472 A | 10/1988 | Homsy et al. |
| 4,795,469 A | 1/1989 | Oh |
| 4,805,602 A | 2/1989 | Puno et al. |
| 4,863,477 A | 9/1989 | Monson |
| 4,904,260 A | 2/1990 | Ray et al. |
| 4,911,718 A | 3/1990 | Lee et al. |
| 4,917,701 A | 4/1990 | Morgan |
| 4,932,975 A | 6/1990 | Main et al. |
| 4,950,270 A | 8/1990 | Bowman et al. |
| 4,955,916 A | 9/1990 | Carignan et al. |
| 4,957,495 A | 9/1990 | Kluger |
| 4,987,904 A | 1/1991 | Wilson |
| 5,000,165 A | 3/1991 | Watanabe |
| 5,015,255 A | 5/1991 | Kuslich |
| 5,019,081 A | 5/1991 | Watanabe |
| 5,047,055 A | 9/1991 | Bao et al. |
| 5,062,845 A | 11/1991 | Kuslich et al. |
| 5,070,623 A | 12/1991 | Barnes |
| 5,071,437 A | 12/1991 | Steffee |
| 5,092,866 A | 3/1992 | Breard et al. |
| 5,098,434 A | 3/1992 | Serbousek |
| 5,108,399 A | 4/1992 | Eitenmuller et al. |
| 5,129,900 A | 7/1992 | Asher et al. |
| 5,147,404 A | 9/1992 | Downey |
| 5,171,280 A | 12/1992 | Baumgartner |
| 5,192,326 A | 3/1993 | Bao et al. |
| 5,258,031 A | 11/1993 | Salib et al. |
| 5,261,910 A | 11/1993 | Warden et al. |
| 5,284,655 A | 2/1994 | Bogdansky et al. |
| 5,300,073 A | 4/1994 | Ray et al. |
| 5,303,480 A | 4/1994 | Chek |
| 5,306,308 A | 4/1994 | Gross et al. |
| 5,306,309 A | 4/1994 | Wagner et al. |
| 5,312,409 A | 5/1994 | McLaughlin et al. |
| 5,314,429 A | 5/1994 | Goble |
| 5,314,476 A | 5/1994 | Prewett et al. |
| 5,314,486 A | 5/1994 | Zang et al. |
| 5,314,489 A | 5/1994 | Hoffman et al. |
| 5,314,492 A | 5/1994 | Hamilton et al. |
| 5,329,933 A | 7/1994 | Graf |
| 5,334,203 A | 8/1994 | Wagner |
| 5,348,026 A | 9/1994 | Davidson |
| 5,350,380 A | 9/1994 | Goble et al. |
| 5,360,448 A | 11/1994 | Thramann |
| 5,370,697 A | 12/1994 | Baumgartner |
| 5,401,269 A | 3/1995 | Buttner-Janz et al. |
| 5,405,390 A | 4/1995 | O'Leary et al. |
| 5,413,576 A | 5/1995 | Rivard |
| 5,415,659 A | 5/1995 | Lee et al. |
| 5,415,661 A | 5/1995 | Holmes |
| 5,425,773 A | 6/1995 | Boyd et al. |
| 5,437,669 A | 8/1995 | Yuan et al. |
| 5,437,672 A | 8/1995 | Alleyne |
| 5,443,483 A | 8/1995 | Kirsch |
| 5,445,639 A | 8/1995 | Kuslich et al. |
| 5,458,641 A | 10/1995 | Ramirez Jimenez |
| 5,458,642 A | 10/1995 | Beer et al. |
| 5,458,643 A | 10/1995 | Oka et al. |
| 5,470,333 A | 11/1995 | Ray |
| 5,474,551 A | 12/1995 | Finn et al. |
| 5,474,555 A | 12/1995 | Puno et al. |
| 5,491,882 A | 2/1996 | Walston et al. |
| 5,496,318 A | 3/1996 | Howland et al. |
| 5,501,684 A | 3/1996 | Schlapfer et al. |
| 5,507,823 A | 4/1996 | Walston et al. |
| 5,510,396 A | 4/1996 | Prewett et al. |
| 5,514,180 A | 5/1996 | Heggeness et al. |
| 5,527,312 A | 6/1996 | Ray |
| 5,534,028 A | 7/1996 | Bao et al. |
| 5,534,030 A | 7/1996 | Navarro et al. |
| 5,545,229 A | 8/1996 | Parsons et al. |
| 5,556,431 A | 9/1996 | Buttner-Janz |
| 5,562,738 A | 10/1996 | Boyd et al. |
| 5,569,247 A | 10/1996 | Morrison |
| 5,571,189 A | 11/1996 | Kuslich |
| 5,571,191 A | 11/1996 | Fitz |
| 5,575,792 A | 11/1996 | Errico et al. |
| 5,577,995 A | 11/1996 | Walker et al. |
| 5,587,695 A | 12/1996 | Warmerdam |
| 5,599,311 A | 2/1997 | Raulerson |
| 5,603,713 A | 2/1997 | Aust et al. |
| 5,609,641 A | 3/1997 | Johnson et al. |
| 5,643,263 A | 7/1997 | Simonson |
| 5,645,597 A | 7/1997 | Krapiva |
| 5,645,599 A | 7/1997 | Samani |
| 5,649,930 A | 7/1997 | Kertzner |
| 5,653,762 A | 8/1997 | Pisharodi |
| 5,658,338 A | 8/1997 | Tullos et al. |
| 5,662,651 A | 9/1997 | Tornier et al. |
| 5,672,175 A | 9/1997 | Martin |
| 5,674,295 A | 10/1997 | Ray et al. |
| 5,674,296 A | 10/1997 | Bryan et al. |
| 5,676,701 A | 10/1997 | Yuan et al. |
| 5,678,317 A | 10/1997 | Stefanakos |
| 5,683,391 A | 11/1997 | Boyd |
| 5,683,392 A | 11/1997 | Richelsoph et al. |
| 5,683,464 A | 11/1997 | Wagner et al. |
| 5,683,466 A | 11/1997 | Vitale |
| 5,688,274 A | 11/1997 | Errico et al. |
| 5,690,630 A | 11/1997 | Errico et al. |
| 5,700,268 A | 12/1997 | Bertin |
| 5,702,450 A | 12/1997 | Bisserie |
| 5,704,941 A | 1/1998 | Jacober et al. |
| 5,716,415 A | 2/1998 | Steffee |
| 5,725,527 A | 3/1998 | Biedermann et al. |
| 5,733,284 A | 3/1998 | Martin |
| 5,738,585 A | 4/1998 | Hoyt, III et al. |
| 5,741,255 A | 4/1998 | Krag et al. |
| 5,741,261 A | 4/1998 | Moskovitz et al. |
| 5,766,253 A | 6/1998 | Brosnahan, III |
| 5,776,135 A | 7/1998 | Errico et al. |
| 5,782,833 A | 7/1998 | Haider |
| 5,797,911 A | 8/1998 | Sherman et al. |
| 5,800,433 A | 9/1998 | Benzel et al. |
| 5,810,816 A * | 9/1998 | Roussouly et al. ........... 606/246 |
| 5,824,093 A | 10/1998 | Ray et al. |
| 5,824,094 A | 10/1998 | Serhan et al. |
| 5,827,289 A | 10/1998 | Reiley et al. |
| 5,836,948 A | 11/1998 | Zucherman et al. |
| 5,860,977 A | 1/1999 | Zucherman et al. |
| 5,863,293 A | 1/1999 | Richelsoph |
| 5,865,846 A | 2/1999 | Bryan et al. |
| 5,866,113 A | 2/1999 | Hendriks et al. |
| 5,868,745 A | 2/1999 | Alleyne |
| 5,879,350 A | 3/1999 | Sherman et al. |
| 5,879,396 A | 3/1999 | Walston et al. |
| 5,885,285 A | 3/1999 | Simonson |
| 5,885,286 A | 3/1999 | Sherman et al. |
| 5,891,145 A | 4/1999 | Morrison et al. |
| 5,893,889 A | 4/1999 | Harrington |
| RE36,221 E | 6/1999 | Breard et al. |
| 5,947,893 A | 9/1999 | Agrawal et al. |
| 5,947,965 A | 9/1999 | Bryan |
| 5,964,760 A | 10/1999 | Richelsoph |
| 5,984,926 A | 11/1999 | Jones |
| 6,001,130 A | 12/1999 | Bryan et al. |
| 6,004,353 A | 12/1999 | Masini |
| 6,010,503 A | 1/2000 | Richelsoph et al. |
| 6,014,588 A | 1/2000 | Fitz |
| 6,019,759 A | 2/2000 | Rogozinski |
| 6,019,792 A | 2/2000 | Cauthen |

| Patent/Pub No. | Date | Name |
|---|---|---|
| 6,022,350 A | 2/2000 | Ganem |
| 6,039,763 A | 3/2000 | Shelokov |
| 6,048,342 A | 4/2000 | Zucherman et al. |
| 6,050,997 A | 4/2000 | Mullane |
| 6,053,917 A | 4/2000 | Sherman et al. |
| 6,063,121 A | 5/2000 | Xavier et al. |
| 6,066,325 A | 5/2000 | Wallace et al. |
| 6,068,630 A | 5/2000 | Zucherman et al. |
| RE36,758 E | 6/2000 | Fitz |
| 6,074,391 A | 6/2000 | Metz-Stavenhagen et al. |
| 6,077,262 A | 6/2000 | Schläpfer et al. |
| 6,080,157 A | 6/2000 | Cathro et al. |
| 6,086,590 A | 7/2000 | Margulies et al. |
| 6,090,111 A | 7/2000 | Nichols |
| 6,113,600 A | 9/2000 | Drummond et al. |
| 6,113,637 A | 9/2000 | Gill et al. |
| 6,120,510 A | 9/2000 | Albrektsson et al. |
| 6,132,430 A | 10/2000 | Wagner |
| 6,132,462 A | 10/2000 | Li |
| 6,132,464 A | 10/2000 | Martin |
| 6,132,465 A | 10/2000 | Ray et al. |
| 6,165,177 A | 12/2000 | Wilson et al. |
| 6,190,388 B1 | 2/2001 | Michelson et al. |
| 6,193,724 B1 | 2/2001 | Chan |
| 6,193,758 B1 | 2/2001 | Huebner |
| 6,200,322 B1 | 3/2001 | Branch et al. |
| 6,214,012 B1 | 4/2001 | Karpman et al. |
| 6,224,602 B1 | 5/2001 | Hayes |
| 6,231,575 B1 | 5/2001 | Krag |
| 6,248,105 B1 | 6/2001 | Schläpfer et al. |
| 6,280,443 B1 | 8/2001 | Gu et al. |
| 6,290,703 B1 | 9/2001 | Ganem |
| 6,293,949 B1 | 9/2001 | Justis et al. |
| 6,302,890 B1 | 10/2001 | Leone, Jr. |
| 6,309,391 B1 | 10/2001 | Crandall et al. |
| 6,312,431 B1 | 11/2001 | Asfora |
| 6,340,361 B1 | 1/2002 | Kraus et al. |
| 6,340,477 B1 | 1/2002 | Anderson |
| 6,342,054 B1 | 1/2002 | Mata |
| 6,361,506 B1 | 3/2002 | Saenger et al. |
| 6,368,320 B1 | 4/2002 | Le Couedic et al. |
| 6,419,703 B1 | 7/2002 | Fallin et al. |
| 6,440,169 B1 | 8/2002 | Elberg et al. |
| 6,443,954 B1 | 9/2002 | Bramlet et al. |
| 6,451,021 B1 | 9/2002 | Ralph et al. |
| 6,471,705 B1 | 10/2002 | Biedermann et al. |
| 6,514,253 B1 | 2/2003 | Yao |
| 6,520,963 B1 | 2/2003 | McKinley |
| 6,524,315 B1 | 2/2003 | Selvitelli et al. |
| 6,540,749 B2 | 4/2003 | Schäfer et al. |
| 6,547,790 B2 | 4/2003 | Harkey, III et al. |
| 6,554,843 B1 | 4/2003 | Ou |
| 6,565,565 B1 | 5/2003 | Yuan et al. |
| 6,565,572 B2 | 5/2003 | Chappius |
| 6,565,605 B2 | 5/2003 | Goble et al. |
| 6,572,617 B1 | 6/2003 | Senegas |
| 6,579,319 B2 | 6/2003 | Goble et al. |
| 6,585,740 B2 | 7/2003 | Schlapfer et al. |
| 6,585,769 B1 | 7/2003 | Muhanna et al. |
| 6,607,530 B1 | 8/2003 | Carl et al. |
| 6,610,091 B1 | 8/2003 | Reiley |
| 6,619,091 B2 | 9/2003 | Heffe |
| 6,623,485 B2 | 9/2003 | Doubler et al. |
| 6,626,909 B2 | 9/2003 | Chin |
| 6,632,226 B2 | 10/2003 | Chan |
| 6,638,281 B2 | 10/2003 | Gorek |
| 6,638,321 B1 | 10/2003 | Genet et al. |
| 6,645,214 B2 | 11/2003 | Brown et al. |
| 6,648,891 B2 | 11/2003 | Kim |
| 6,669,698 B1 | 12/2003 | Tromanhauser et al. |
| 6,669,729 B2 | 12/2003 | Chin |
| 6,712,818 B1 | 3/2004 | Michelson |
| 6,712,849 B2 | 3/2004 | Re et al. |
| 6,736,815 B2 | 5/2004 | Ginn |
| 6,749,361 B2 | 6/2004 | Hermann et al. |
| 6,761,698 B2 | 7/2004 | Shibata et al. |
| 6,761,720 B1 | 7/2004 | Senegas |
| 6,770,095 B2 | 8/2004 | Grinberg et al. |
| 6,783,527 B2 | 8/2004 | Drewry et al. |
| 6,790,233 B2 | 9/2004 | Brodke et al. |
| 6,793,678 B2 | 9/2004 | Hawkins |
| 6,802,844 B2 | 10/2004 | Ferree |
| 6,811,567 B2 | 11/2004 | Reiley |
| 6,860,884 B2 * | 3/2005 | Shirado et al. ............... 606/330 |
| 6,902,580 B2 | 6/2005 | Fallin et al. |
| 6,949,123 B2 | 9/2005 | Reiley |
| 6,974,478 B2 | 12/2005 | Reiley |
| 6,979,299 B2 | 12/2005 | Peabody et al. |
| 7,011,658 B2 | 3/2006 | Young |
| 7,044,969 B2 | 5/2006 | Errico et al. |
| 7,051,451 B2 | 5/2006 | Augostino et al. |
| 7,220,262 B1 | 5/2007 | Hynes |
| 7,294,127 B2 | 11/2007 | Leung et al. |
| 7,302,288 B1 | 11/2007 | Schellenberg |
| 7,309,338 B2 | 12/2007 | Cragg |
| 7,445,635 B2 | 11/2008 | Fallin et al. |
| 7,547,324 B2 | 6/2009 | Cragg et al. |
| 2001/0012938 A1 | 8/2001 | Zucherman et al. |
| 2001/0020170 A1 | 9/2001 | Zucherman et al. |
| 2002/0013585 A1 | 1/2002 | Gournay et al. |
| 2002/0013588 A1 | 1/2002 | Landry et al. |
| 2002/0029039 A1 | 3/2002 | Zucherman et al. |
| 2002/0042613 A1 | 4/2002 | Mata |
| 2002/0049446 A1 | 4/2002 | Harkey, III et al. |
| 2002/0052603 A1 | 5/2002 | Nichols et al. |
| 2002/0065557 A1 | 5/2002 | Goble et al. |
| 2002/0068975 A1 | 6/2002 | Teitelbaum et al. |
| 2002/0082601 A1 | 6/2002 | Toyama et al. |
| 2002/0120272 A1 | 8/2002 | Yuan et al. |
| 2002/0123752 A1 | 9/2002 | Schultheiss et al. |
| 2002/0123806 A1 | 9/2002 | Reiley |
| 2002/0143335 A1 | 10/2002 | von Hoffmann et al. |
| 2002/0151895 A1 | 10/2002 | Soboleski et al. |
| 2003/0004572 A1 | 1/2003 | Goble et al. |
| 2003/0028250 A1 | 2/2003 | Reiley et al. |
| 2003/0040797 A1 | 2/2003 | Fallin et al. |
| 2003/0055427 A1 | 3/2003 | Graf |
| 2003/0069603 A1 | 4/2003 | Little et al. |
| 2003/0125740 A1 | 7/2003 | Khanna |
| 2003/0171754 A1 | 9/2003 | Del Medico |
| 2003/0181914 A1 | 9/2003 | Johnson et al. |
| 2003/0191532 A1 | 10/2003 | Goble et al. |
| 2003/0195631 A1 | 10/2003 | Ferree |
| 2003/0204259 A1 | 10/2003 | Goble et al. |
| 2003/0204261 A1 | 10/2003 | Eisermann et al. |
| 2003/0233148 A1 | 12/2003 | Ferree |
| 2004/0006391 A1 | 1/2004 | Reiley |
| 2004/0049205 A1 | 3/2004 | Lee et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0059429 A1 | 3/2004 | Amin et al. |
| 2004/0111154 A1 | 6/2004 | Reiley |
| 2004/0116927 A1 | 6/2004 | Graf |
| 2004/0127989 A1 | 7/2004 | Dooris et al. |
| 2004/0143264 A1 | 7/2004 | McAfee |
| 2004/0204710 A1 | 10/2004 | Patel et al. |
| 2004/0204718 A1 | 10/2004 | Hoffman |
| 2004/0230201 A1 | 11/2004 | Yuan et al. |
| 2004/0230304 A1 | 11/2004 | Yuan et al. |
| 2004/0260305 A1 | 12/2004 | Gorensek et al. |
| 2005/0010291 A1 | 1/2005 | Stinson et al. |
| 2005/0015146 A1 | 1/2005 | Louis et al. |
| 2005/0027361 A1 | 2/2005 | Reiley |
| 2005/0043799 A1 | 2/2005 | Reiley |
| 2005/0049705 A1 | 3/2005 | Hale et al. |
| 2005/0055096 A1 | 3/2005 | Serhan et al. |
| 2005/0080428 A1 | 4/2005 | White |
| 2005/0080486 A1 | 4/2005 | Fallin et al. |
| 2005/0085912 A1 | 4/2005 | Arnin et al. |
| 2005/0102028 A1 | 5/2005 | Arnin et al. |
| 2005/0119748 A1 | 6/2005 | Reiley et al. |
| 2005/0131406 A1 | 6/2005 | Reiley et al. |

| | | | |
|---|---|---|---|
| 2005/0137705 | A1 | 6/2005 | Reiley |
| 2005/0137706 | A1 | 6/2005 | Reiley |
| 2005/0143818 | A1 | 6/2005 | Yuan et al. |
| 2005/0149190 | A1 | 7/2005 | Reiley |
| 2005/0177240 | A1 | 8/2005 | Blain |
| 2005/0187560 | A1 | 8/2005 | Dietzel et al. |
| 2005/0192589 | A1 | 9/2005 | Raymond et al. |
| 2005/0234552 | A1 | 10/2005 | Reiley |
| 2005/0235508 | A1 | 10/2005 | Augostino et al. |
| 2005/0240264 | A1 | 10/2005 | Tokish, Jr. et al. |
| 2005/0240265 | A1 | 10/2005 | Kuiper et al. |
| 2005/0240266 | A1 | 10/2005 | Kuiper et al. |
| 2005/0251256 | A1 | 11/2005 | Reiley |
| 2005/0261770 | A1 | 11/2005 | Kuiper et al. |
| 2005/0267579 | A1 | 12/2005 | Reiley et al. |
| 2005/0283238 | A1 | 12/2005 | Reiley |
| 2006/0009847 | A1 | 1/2006 | Reiley |
| 2006/0009848 | A1 | 1/2006 | Reiley |
| 2006/0009849 | A1 | 1/2006 | Reiley |
| 2006/0029186 | A1 | 2/2006 | De Villiers et al. |
| 2006/0041311 | A1 | 2/2006 | McLeer |
| 2006/0052785 | A1 | 3/2006 | Augostino et al. |
| 2006/0058791 | A1 | 3/2006 | Broman et al. |
| 2006/0079895 | A1 | 4/2006 | McLeer |
| 2006/0085072 | A1 | 4/2006 | Funk et al. |
| 2006/0085075 | A1 | 4/2006 | McLeer |
| 2006/0100709 | A1 | 5/2006 | Reiley et al. |
| 2006/0122703 | A1 | 6/2006 | Aebi et al. |
| 2006/0149375 | A1 | 7/2006 | Yuan et al. |
| 2006/0184180 | A1 | 8/2006 | Augostino et al. |
| 2006/0265070 | A1 | 11/2006 | Stinson et al. |
| 2007/0079517 | A1 | 4/2007 | Augostino et al. |
| 2007/0088358 | A1 | 4/2007 | Yuan et al. |

FOREIGN PATENT DOCUMENTS

| | | |
|---|---|---|
| EP | 1103226 | 5/2001 |
| EP | 1205152 A1 | 5/2002 |
| EP | 1254639 A1 | 11/2002 |
| FR | 2726459 | 5/1996 |
| FR | 2749155 | 12/1997 |
| FR | 2844180 | 3/2004 |
| IE | S970323 | 6/1998 |
| JP | 59010807 A | 1/1984 |
| JP | 10082605 A | 3/1998 |
| JP | 10179622 A | 7/1998 |
| WO | WO 95/05783 A1 | 3/1995 |
| WO | WO 96/00049 A1 | 1/1996 |
| WO | WO 98/48717 A1 | 11/1998 |
| WO | WO 98/56301 A1 | 12/1998 |
| WO | WO 99/05995 A1 | 2/1999 |
| WO | WO 99/23963 A1 | 5/1999 |
| WO | WO 99/60957 A1 | 12/1999 |
| WO | WO 99/65412 A1 | 12/1999 |
| WO | WO 00/38582 A1 | 7/2000 |
| WO | WO 00/62684 A1 | 10/2000 |
| WO | WO 01/06939 A1 | 2/2001 |
| WO | WO 01/15638 A1 | 3/2001 |
| WO | WO 01/28442 A1 | 4/2001 |
| WO | WO 01/30248 A1 | 5/2001 |
| WO | WO 01/39678 A1 | 6/2001 |
| WO | WO 01/67972 A2 | 9/2001 |
| WO | WO 01/97721 A2 | 12/2001 |
| WO | WO 02/00270 A1 | 1/2002 |
| WO | WO 02/00275 A1 | 1/2002 |
| WO | WO 02/02024 A1 | 1/2002 |
| WO | WO 02/02158 A1 | 1/2002 |
| WO | WO 02/24149 A2 | 3/2002 |
| WO | WO 02/34150 A2 | 5/2002 |
| WO | WO 02/43603 A1 | 6/2002 |
| WO | WO 02/071960 A1 | 9/2002 |
| WO | WO 02/089712 A1 | 11/2002 |
| WO | WO 03/020143 A1 | 3/2003 |
| WO | WO 03/041618 A2 | 5/2003 |
| WO | WO 03/075805 A1 | 9/2003 |
| WO | WO 03/101350 A1 | 12/2003 |
| WO | WO 2004/071358 A1 | 8/2004 |
| WO | WO 2004/103227 A1 | 12/2004 |
| WO | WO 2004/103228 A1 | 12/2004 |
| WO | WO 2005/009301 A1 | 2/2005 |

OTHER PUBLICATIONS

Eichholz, K.M. et al. Complications of Revision Spinal Surgery. *Neurosurg Focus*. Sep. 2003; 15(3): pp. 1-4.

Farfan, H.F. Effects of Torsion on the Intervertebral Joints. *The Canadian Journal of Surgery*. Jul. 1969; 12(3):336-41.

Farfan, H.F. The Pathological Anatomy of Degenerative Spondylolisthesis. A Cadaver Study. *Spine*. Sep.-Oct. 1980; 5(5):412-8.

Farfan, H.F. et al. The Relation of Facet Orientation to Intervertebral Disc Failure. *The Canadian Journal of Surgery*. Apr. 1967; 10(2):179-85.

Fosbinder, R.A. et al. *Essentials of Radiologic Science*. The McGraw-Hill Companies; 2002.

Goh, J.C. et al. Influence of PLIF cage size on lumbar spine stability. *Spine*. Jan. 2000; 25(1) Medline abstract (one page).

Guyer, R. et al. Impliant: Motion Preservation through Total Posterior-Element Replacement. May 7, 2004; Presentation held at Hofburg Center, Vienna, Austria, (2 pages).

Head, W.C. Wagner surface replacement arthroplasty of the hip. Analysis of fourteen failures in forty-one hips. *J Bone Joint Surg. Am*. Mar. 1981, 63(3), Medline abstract (one page).

Khoo, L.T. et al. A biomechanical analysis of the effects of lumbar fusion on the adjacent vetebral motion segment. Proceedings of the 2000 Annual Meeting of the North American Spine Society, New Orleans, pp. 127-128.

Kirkaldy-Willis, W.H. et al. Pathology and Pathogenesis of Lumbar Spondylosis and Stenosis. *Spine*. Dec. 1978; 3(4):319-28.

Kotani, Y. et al. The effects of spinal fixation and destabilization on the biomechanical and histologic properties of spinal ligaments. An in vivo study. *Spine*, Mar. 15, 1998; 23(6), Medline abstract (2 pages).

Kulkarni, et al. Accelerated Spondylotic Changes Adjacent to the Fused Segment Following Central Cervical Corpectomy: Magnetic Resonance Imaging Study Evidence. *J. Neurosurg (Spine 1)*. 2004; 100: 2-6.

Lam, K. N., et al. *X-ray Diagnosis: A Physician's Approach*. Springer-Verlag; 1998.

Lemaire, J.P. et al. Intervertebral disc prosthesis: results and prospects for the year 2000, Clinical Orthopaedics and Related Research. 1997; No. 337, pp. 64-76.

Lombardi, J.S. et al. Treatment of Degenerative Spondylolisthesis. *Spine*. 1985; 10(9): 821-7.

McMillin, C. R. et al. Artificial Spinal Discs with up to Five Years Follow-up. 20th Annual Meeting of the Society for Biomaterials (Abstract). 1994; p. 89.

Nagata, H. et al. The effects of immobilization of long segments of the spine on the adjacent and distal facet force and lumbrosacral motion. *Spine*. Dec. 1993; 18(16):2471-2479, (9 pages).

Nibu, K. et al. Multidirectional stabilizing potential of BAK interbody spinal fusion system for anterior surgery. *J. Spinal Discord*. Aug. 1997; 10(4), Medline abstract (one page).

Posner, I. et al. A Biomechanical Analysis of the Clinical Stability of the Lumbar and Lumbosacral Spine. *Spine*. 1982; 7(4): 374-389.

Rosenberg, N.J. Degenerative Spondylolisthesis. Predisposing Factors. *J Bone Joint Surg Am*. 1975; 57-A(4): 467-74.

Sacher, R. Impliant Brochure for presentation at MedTech Insight Conference (Oct. 31, 2003). Boston, MA. pp. 93-94.

Slone, R. M. et al. *Body CT: A Practical Approach*. The McGraw-Hill Companies; 1999.

Stout, G. H. et al. *X-Ray Structure Determination: A Practical Guide*. 2nd Edition. John Wiley & Sons; 1989.

Szpalski, M. et al. Spine Arthroplasty: A Historical Review. *Eur Spine J*. 2002; 11(Suppl. 2): S65-S84.

Tsantrizos, A. et al. Segmental stability and compressive strength of posterior lumbar interbody fusion implants. *Spine*. Aug. 1, 2000; 25(15), Medline abstract (one page).

UCR Pedicle Screw System from SeaSpine (information available at http://www.seaspine.com/UCR_Pedicle_Screw_System.html). Accessed Dec. 5, 2005.

Victrex of Lancashire, Great Britain. (information on Victrex available at http://www.matweb.com). Accessed Dec. 5, 2005.

Ochoa et al.; U.S. Appl. No. 12/377,546 entitled "Spinal implant," filed Feb. 13, 2009.

Hewko, Brian; U.S. Appl. No. 12/377,552 entitled "Spinal implant," filed Feb. 13, 2009.
Reiley et al; U.S. Appl. No. 11/577,923 entitled "Crossbar spinal prosthesis having a modular design and systems for treating spinal pathologies" filed Apr. 25, 2007.
McLeer, Thomas, U.S. Appl. No. 11/934,724 entitled "Polymeric Joint Complex and Methods of Use" filed Nov. 2, 2007.
McLeer, Thomas, U.S. Appl. No. 11/934,720 entitled "Polymeric Joint Complex and Methods of Use" filed Nov. 2, 2007.
McLeer, Thomas, U.S. Appl. No. 11/934,719 entitled "Polymeric Joint Complex and Methods of Use" filed Nov. 2, 2007.
Reiley, Mark, U.S. Appl. No. 11/934,713 entitled "Facet arthroplasty devices and methods" filed Nov. 2, 2007.
Reiley, Mark, U.S. Appl. No. 11/939,540 entitled "Facet arthroplasty devices and methods" filed Nov. 13, 2007.
Reiley, Mark, U.S. Appl. No. 11/943,458 entitled "Facet arthroplasty devices and methods" filed Nov. 20, 2007.
Reiley, Mark, U.S. Appl. No. 11/949,007 entitled "Facet arthroplasty devices and methods" filed Nov. 30, 2007.
Reiley, Mark, U.S. Appl. No. 11/949,000 entitled "Facet arthroplasty devices and methods" filed Nov. 30, 2007.
Reiley et al.; U.S. Appl. No. 11/948,963 entitled "Prostheses, systems and methods for replacement of natural facet joints with artificial facet joint surfaces" filed Nov. 30, 2007.
Reiley, Mark, U.S. Appl. No. 11/957,208 entitled "Facet arthroplasty devices and methods" filed Dec. 14, 2007.
Reiley et al.; U.S. Appl. No. 11/957,315 entitled "Prostheses, systems and methods for replacement of natural facet joints with artificial facet joint surfaces" filed Dec. 14, 2007.
Reiley, Mark; U.S. Appl. No. 11/957,175 entitled "Facet arthroplasty devices and methods" filed Dec. 14, 2007.
Reiley et al.; U.S. Appl. No. 11/957,290 entitled "Prostheses, systems and methods for replacement of natural facet joints with artificial facet joint surfaces" filed Dec. 14, 2007.
Reiley, Mark; U.S. Appl. No. 11/956,961 entitled "Facet arthroplasty devices and methods" filed Dec. 14, 2007.
Reiley, Mark; U.S. Appl. No. 11/957,149 entitled "Facet arthroplasty devices and methods" filed Dec. 14, 2007.
Reiley, Mark; U.S. Appl. No. 11/957,061 entitled "Facet arthroplasty devices and methods" filed Dec. 14, 2007.
Reiley et al.; U.S. Appl. No. 11/957,259 entitled "Prostheses, systems and methods for replacement of natural facet joints with artificial facet joint surfaces" filed Dec. 14, 2007.
Reiley, Mark; U.S. Appl. No. 12/016,177 entitled "Facet arthroplasty devices and methods" filed Jan. 17, 2008.
Kuiper et al.; U.S. Appl. No. 11/948,994 entitled "Crossbar spinal prosthesis having a modular design and related implantation methods" filed Nov. 30, 2007.
Kuiper et al.; U.S. Appl. No. 11/948,973 entitled "Crossbar spinal prosthesis having a modular design and related implantation methods" filed Nov. 30, 2007.
Kuiper et al.; U.S. Appl. No. 11/957,303 entitled "Crossbar spinal prosthesis having a modular design and related implantation methods" filed Nov. 30, 2007.
McLeer, Thomas; U.S. Appl. No. 11/952,988 entitled "Polymeric joint complex and methods of use" filed Dec. 7, 2007.
Yuan et al.; U.S. Appl. No. 12/027,899 entitled "Prostheses, tools and methods for replacement of natural facet joints with artificial facet joint surfaces," filed Feb. 7, 2008.

Reiley et al; U.S. Appl. No. 12/058,403 entitled "Polyaxial adjustment of facet joint prostheses," filed Mar. 28, 2008.
Yuan et al; U.S. Appl. No. 11/636,252 entitled "Prostheses, Tools, and Methods for Replacement of Natural Facet Joints with Artificial Facet Joint Surfaces" filed Dec. 8, 2006.
Broman et al; U.S. Appl. No. 11/642,417, entitled "Arthroplasty revision system and method" filed Dec. 20, 2006.
Ohrt et al; U.S. Appl. No. 11/724,927 entitled "Facet and disc arthroplasty system and method" filed Mar. 15, 2007.
Kuiper et al; U.S. Appl. No. 11/635,853, entitled "Crossbar Spinal Prosthesis Having a Modular Design and Related Implantation Methods", filed Dec. 8, 2006.
Reiley et al; U.S. Appl. No. 11/746,027 entitled "Facet Arthroplasty Devices and Methods," filed May 8, 2007.
Reiley et al; U.S. Appl. No. 11/577,872 entitled "Facet Joint Prosthesis" which entered the U.S. from the National Phase Apr. 24, 2007.
Reiley et al; U.S. Appl. No. 11/577,923 entitled "Facet Joint Prostheses" filed Apr. 25, 2007.
Kuiper et al; U.S. Appl. No. 11/577,964 entitled "Crossbar Spinal Prosthesis Having a Modular Design and Systems for Treating Spinal Pathologies," filed Apr. 25, 2007.
Kuiper et al; U.S. Appl. No. 11/577,967 entitled "Crossbar Spinal Prosthesis having a Modular Design and Systems for Treating Spinal Pathologies," filed Apr. 25, 2007.
Reiley, Mark; U.S. Appl. No. 11/750,981 entitled "Facet Arthroplasty Device and Methods," filed May 18, 2007.
Berg, et al; U.S. Appl. No. 11/800,895 entitled "Minimally Invasive Spine Restoration Systems, Devices, Methods, and Kits," filed May 7, 2007.
Quest et al.; U.S. Appl. No. 12/099,068 entitled "Measurement and trialing system and methods for orthopedic device component selection," filed Apr. 7, 2008.
Reiley, Mark; U.S. Appl. No. 12/176,280 entitled "Facet arthroplasty devices and methods," filed Jul. 18, 2008.
Yuan et al; U.S. Appl. No. 12/163,738 entitled "Prostheses, tools and methods for replacement of natural joints with artificial facet joint surfaces," filed Jun. 27, 2008.
Funk et al; U.S. Appl. No. 12/186,461 entitled "Implantable orthopedic device component selection instrument and methods," filed Aug. 5, 2008.
Reiley, Mark; U.S. Appl. No. 11/839,434 entitled "Facet arthroplasty devices and methods", filed Aug. 15, 2007.
Reiley, Mark; U.S. Appl. No. 11/824,012 entitled "Facet arthroplasty device end methods," filed Jun. 29, 2007.
Reiley, Mark; U.S. Appl. No. 11/831,870 entitled "Prostheses systems and methods for replacement of natural facet Johns with artificial facet joint surfaces," filed Jul. 31, 2007.
Ralph at al; U.S. Appl. No. 11/837,335 entitled "Angled Washer Polyaxial Connection for Dynamic Spine Prosthesis," filed Aug. 10, 2007.
Reiley, Mark; U.S. Appl. No. 11/775,174 entitled "Facet arthroplasty devices end methods," filed Jul. 9, 2007.
Stone at al; U.S. Appl. No. 11/881,239 entitled "Facet Replacement Device Removal and Revision Systems and Methods" filed Sep. 25, 2007.

* cited by examiner

US 8,523,907 B2

PROSTHESES, TOOLS AND METHODS FOR REPLACEMENT OF NATURAL FACET JOINTS WITH ARTIFICIAL FACET JOINT SURFACES

CROSS-REFERENCE

This application is a continuation application of Ser. No. 10/615,417, filed Jul. 8, 2003 now U.S. Pat. No. 7,074,238, which is incorporated herein by reference in its entirety and to which application we claim priority under 35 USC §120.

FIELD OF THE INVENTION

This invention relates to prostheses for treating various types of spinal pathologies, as well as to methods of treating spinal pathologies.

BACKGROUND OF THE INVENTION

I. Vertebral Anatomy

As FIG. 1 shows, the human spinal column 10 is comprised of a series of thirty-three stacked vertebrae 12 divided into five regions. The cervical region includes seven vertebrae 12, known as C1-C7. The thoracic region includes twelve vertebrae 12, known at T1-T12. The lumbar region contains five vertebrae 12, known as L1-L5. The sacral region is comprised of five vertebrae 12, known as S1-S5. The coccygeal region contains four vertebrae 12, known as Co1-Co4.

FIG. 2 shows a normal human lumbar vertebra 12. Although the lumbar vertebrae 12 vary somewhat according to location, they share many features common to most vertebrae 12. Each vertebra 12 includes a vertebral body 14 and posterior elements as follows:

Two short bones, the pedicles 16, extend backward from each side of the vertebral body 14 to form a vertebral arch 18. At the posterior end of each pedicle 16 the vertebral arch 18 flares out into broad plates of bone known as the laminae 20. The laminae 20 fuse with each other to form a spinous process 22. The spinous process 22 serves for muscle and ligamentous attachment. A smooth transition from the pedicles 16 into the laminae 20 is interrupted by the formation of a series of processes.

Two transverse processes 24 thrust out laterally on each side from the junction of the pedicle 16 with the lamina 20. The transverse processes 24 serve as levers for the attachment of muscles to the vertebrae 12. Four articular processes, two superior 26 and two inferior 28, also rise from the junctions of the pedicles 16 and the 15 laminae 20. The superior articular processes 26 are sharp oval plates of bone rising upward on each side from the union of the pedicle 16 with the lamina 20. The inferior processes 28 are oval plates of bone that extend in an inferior direction on each side.

The superior and inferior articular processes 26 and 28 each have a natural bony structure known as a facet. The superior articular facet 30 faces upward or superiorly, while the inferior articular facet 31 faces downward. As FIG. 3 shows, when adjacent (i.e., cephalad 25 and caudal) vertebrae 12 are aligned, the facets 30 and 31, capped with a smooth articular cartilage, interlock to form a facet joint 32, also known as a zygapophysial joint.

The facet joint 32 is composed of a superior half and an inferior half. The superior half is formed by the vertebral level below the joint 32, and the inferior half is formed by the vertebral level above the joint 32. For example, in the L4-L5 facet joint, the superior portion of the joint is formed by bony structure on the L-5 vertebra (e.g., a superior articular surface and supporting bone on the L-5 vertebra), and the inferior portion of the joint is formed by bony structure on the L-4 vertebra (e.g., an inferior articular surface and supporting bone on the L-4 vertebra).

As also shown in FIG. 3, an intervertebral disc 34 between each pair of vertebrae 12 permits relative movement between vertebrae 12. Thus, the structure and alignment of the vertebrae 12 permit a range of movement of the vertebrae 12 relative to each other.

II. Facet Joint Dysfunction

Back pain, particularly in the "small of the back", or lumbosacral (L4-S1) region, is a common ailment. In many cases, the pain severely limits a person's functional ability and quality of life. Such pain can result from a variety of spinal pathologies.

Through disease or injury, the laminae, spinous process, articular processes, or facets of one or more vertebrae can become damaged, such that the vertebrae no longer articulate or properly align with each other. This can result in an undesired anatomy, pain or discomfort, and loss of mobility.

For example, the vertebral facet joints can be damaged by either traumatic injury or by various disease processes. These disease processes include osteoarthritis, ankylosing spondylolysis, and degenerative spondylolisthesis. The damage to the facet joints often results in pressure on nerves, also called a "pinched" nerve, or nerve compression or impingement. The result is pain, misaligned anatomy, and a corresponding loss of mobility. Pressure on nerves can also occur without facet joint pathology, e.g., a herniated disc.

One type of conventional treatment of facet joint pathology is spinal stabilization, also known as intervertebral stabilization. Intervertebral stabilization prevents relative motion between the vertebrae. By preventing movement, pain can be reduced. Stabilization can be accomplished by various methods.

One method of stabilization is posterior spinal fusion. Another method of stabilization is anterior spinal fusions, fixation of any number of vertebrae to stabilize and prevent movement of the vertebrae.

Another type of conventional treatment is decompressive laninectomy. This procedure involves excision of the laminae to relieve compression of nerves.

These traditional treatments are subject to a variety of limitations and varying success rates. Furthermore, none of the described treatments puts the spine in proper alignment or return the spine to a desired anatomy. In addition, stabilization techniques, by holding the vertebrae in a fixed position, permanently limit the relative motion of the vertebrae, altering spine biomechanics.

SUMMARY OF THE INVENTION

There is a need for prostheses, installation tools, and methods that overcome the problems and disadvantages associated with current strategies and designs in various treatments for spine pathologies.

The invention provides prostheses, installation tools, and methods designed to replace natural facet joints at virtually all spinal levels including L1-L2, L2-L3, L3-L4, L4-L5, L5-S1, T-11-T12, and T12-L1. The prostheses, installation tools, and methods can restore a desired anatomy to a spine and give back to an individual a desired range of relative vertebral motion. The prostheses, installation tools, and methods also can lessen or alleviate spinal pain by relieving the source of nerve compression or impingement.

For the sake of description, the prostheses that embody features of the invention will be called either "cephalad" or "caudal" with relation to the portion of a given natural facet joint they replace. As previously described, a given natural facet joint has a superior half and an inferior half. In anatomical terms, the superior half of the joint is formed by the vertebral level below the joint (which can thus be called the caudal portion of the facet joint, i.e., because it is near the feet). The inferior half of the joint is formed by the vertebral level above the joint (which can thus be called the cephalad portion of the facet joint, i.e., because it is near the head). Thus, a prosthesis that, in use, replaces the caudal portion of a facet joint (i.e., the superior half) will be called a "caudal" prosthesis. Likewise, a prosthesis that, in use, replaces the cephalad portion of a facet joint (i.e., the inferior half) will be called a "cephalad" prosthesis.

One aspect of the invention provides a prosthesis to replace a cephalad portion of a natural facet joint on a vertebra. The prosthesis includes: an artificial facet joint bearing element adapted and configured to replace the cephalad portion of the natural facet joint; and a fixation mechanism (such as a clamp) adapted and configured to attach the artificial facet joint bearing element to the vertebra, the fixation mechanism including a non-invasive support member adapted and configured to attach to a lamina portion of the vertebra, such as substantially at a spinous process location. The support member may be further adapted and configured to be in contact with the lamina portion of the vertebra on at least two opposing sides and possibly four surfaces of the lamina portion of the vertebra. The fixation mechanism is preferably further adapted and configured to attach the artificial facet joint element to the vertebra without blocking access to a pedicle portion of the vertebra.

In some embodiments the support member includes first and second vertebra contact surfaces, the distance between the first and second vertebra contact surfaces being adjustable. At least one of the first and second vertebral contact components may be movable with respect to the other vertebral contact component.

The prosthesis may also include an attachment mechanism attaching the artificial facet joint bearing element to the fixation mechanism. The attachment mechanism may traverse a midline of the vertebra. The attachment mechanism may be adapted and configured such that the artificial facet joint bearing element is movable in a cephalad or caudad direction with respect to the fixation mechanism. In some embodiments the attachment element includes a location element movable in a cephalad or caudad direction with respect to the fixation mechanism.

In some embodiments the artificial facet joint bearing element is a right artificial facet joint bearing element and the natural facet joint is a right natural facet joint, and the prosthesis further includes a left artificial facet joint bearing element adapted and configured to replace a cephalad portion of a left natural facet joint. The right and left artificial facet joint bearing elements may be attached to the attachment element.

Another aspect of the invention provides a prosthesis to replace a cephalad portion of a natural facet joint on a vertebra, including an artificial facet joint bearing element adapted and configured to replace the cephalad portion of the natural facet joint; and a fixation mechanism (such as a clamp) adapted and configured to attach the artificial facet joint bearing element to the vertebra (such as a lamina portion of the vertebra) without penetrating any bone portion of the vertebra. In some embodiments the fixation mechanism may be adapted and configured to be in contact with the attachment portion of the vertebra on at least two opposing sides, and possibly on four surfaces, of the vertebra. The fixation mechanism is preferably further adapted and configured to attach the artificial facet joint element to the vertebra without blocking access to a pedicle portion of the vertebra.

In some embodiments, the fixation mechanism includes first and second vertebra contact surfaces, the distance between the first and second vertebra contact surfaces being adjustable, such as by moving one of first and second vertebral contact components with respect to the other vertebral contact component.

The prosthesis may include an attachment mechanism attaching the artificial facet joint bearing element to the fixation mechanism. In some embodiments, the attachment mechanism disposes the artificial facet joint bearing element caudad from the fixation mechanism. In one embodiment the attachment mechanism traverses a midline of the vertebra. The attachment mechanism may be adapted and configured such that the artificial facet joint bearing element is movable in a cephalad or caudad direction with respect to the fixation mechanism. In some embodiments the fixation mechanism is a first fixation mechanism and the attachment mechanism is adapted and configured to penetrate a bone portion of the vertebra to form a second fixation mechanism attaching the artificial bearing element to the vertebra.

In some embodiments, the artificial facet joint bearing element is a right artificial facet joint bearing element and the natural facet joint is a right natural facet joint, with the prosthesis further including a left artificial facet joint bearing element adapted and configured to replace a cephalad portion of a left natural facet joint.

Another aspect of the invention provides a prosthesis to replace a cephalad portion of a natural facet joint on a vertebra, the prosthesis including an artificial facet joint bearing element adapted and configured to replace the cephalad portion of the natural facet joint; and means for affixing the artificial facet joint bearing element to the vertebra (such as a lamina portion of the vertebra) without penetrating any bone portion of the vertebra. In some embodiments, the means for affixing includes first and second components movable with respect to each other. The prosthesis according to this aspect of the invention may also include means for moving the artificial facet joint bearing element in cephalad and caudad directions with respect to the means for affixing.

In some embodiments, the artificial facet joint bearing element is a right artificial facet joint bearing element and the natural facet joint is a right natural facet joint, with the prosthesis further including a left artificial facet joint bearing element adapted and configured to replace a cephalad portion of a left natural facet joint, and with the means for affixing including means for affixing the right and left artificial facet joint bearing elements to the vertebra. The prosthesis may also include means for moving the right and left artificial facet joint bearing elements in cephalad and caudad directions with respect to the means for affixing. In some embodiments, the prosthesis may also include means for affixing the artificial facet joint bearing element to the vertebra by penetrating a bone portion of the vertebra.

Another aspect of the invention provides a prosthesis to replace right and left cephalad portions of right and left natural facet joints on a vertebra, with the prosthesis including right and left artificial facet joint bearing elements adapted and configured to replace the cephalad portions of the right and left natural facet joints; and a fixation mechanism adapted and configured to attach the artificial facet joint bearing element to a lamina portion of the vertebra without penetrating any bone portion of the vertebra. The prosthesis may also include an attachment mechanism attaching the right and left artificial facet joint bearing elements to the fixation mechanism. The attachment mechanism may be adapted and configured to move the right and left artificial joint bearing elements in a cephalad or caudad direction with respect to the fixation mechanism.

Yet another aspect of the invention provides a method for implanting a cephalad facet joint prosthesis on a vertebra, with the method including the steps of affixing a fixation element to the vertebra (such as a lamina portion of the vertebra) without penetrating any bone portion of the vertebra; and disposing an artificial facet joint bearing element in a predetermined position with respect to the vertebra. In some embodiments the affixing step may include placing a fixation mechanism in contact with an attachment portion of the vertebra on at least two opposing sides of the attachment portion of the vertebra, such as by placing the fixation mechanism in contact with the attachment portion of the vertebra on four surfaces of the attachment portion of the vertebra. The fixation mechanism may include first and second vertebral contact components, with the affixing step including moving one of the first and second vertebral contact components with respect to the other. The affixing step may also include the step of preventing relative movement between the first and second vertebral contact components after the moving step. In some embodiments the affixing step includes affixing a fixation mechanism to the vertebra without blocking access to a pedicle portion of the vertebra.

The disposing step of this aspect of the invention may include fastening the artificial facet joint bearing element to a fixation mechanism, such as by inserting a fastener through the fixation element. The disposing step may also include moving the artificial facet joint bearing element in a cephalad or caudad direction with respect to the vertebra.

In this method, the fixation mechanism may be a first fixation mechanism, with the method further including the step of affixing a second fixation mechanism to the vertebra by penetrating the vertebra (such as by inserting a fastener into a lamina portion of the vertebra) and possibly attaching the second fixation mechanism to the first fixation mechanism. The fastener may be inserted through the fixation element across a midline of the vertebra, and the artificial facet joint bearing element may be attached to the fastener.

In some embodiments of the method, the artificial facet joint bearing element is a right artificial facet joint bearing element, with the disposing step further including disposing a left artificial facet joint bearing element in a predetermined position with respect to the vertebra.

Other features and advantages of the inventions are set forth in the following Description and Drawings, as well as in the appended claims.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Although the disclosure hereof is detailed and exact to enable those skilled in the art to practice the invention, the physical embodiments herein disclosed merely exemplify the invention that may be embodied in other specific structure.

While the preferred embodiment has been described, the details may be changed without departing from the invention, which is defined by the claims.

FIGS. 4-12 show artificial cephalad and caudal facet joint prostheses for replacing a natural facet joint according to one aspect of the invention. The cephalad prosthesis has a bearing element 38 with a bearing surface 40. In this embodiment, bearing surface 40 has a convex shape. Bearing element 38 and bearing surface 40 may be formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts.

Figure 1:
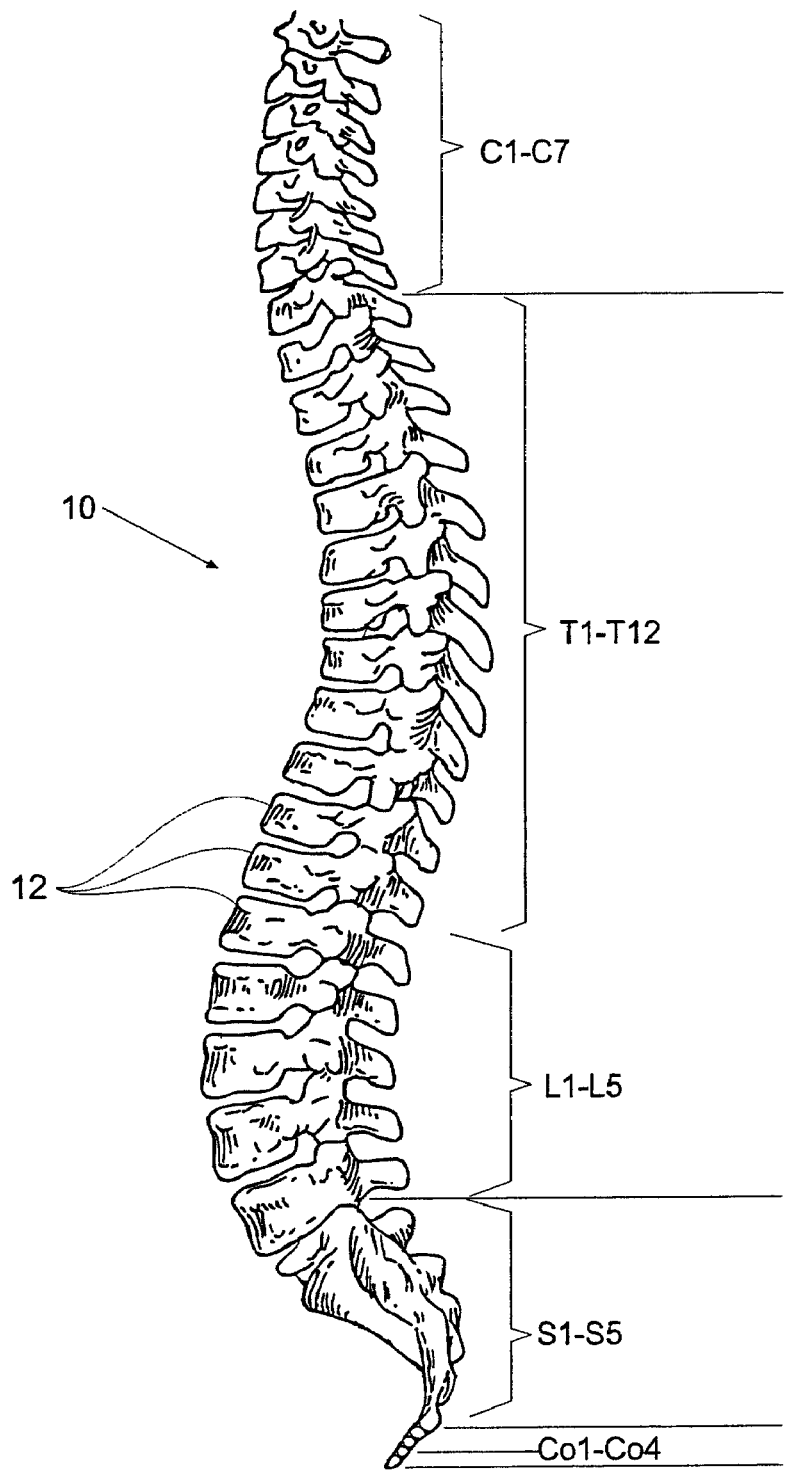
FIG. 1 is a lateral elevation view of a normal human spinal column.
Figure 2:
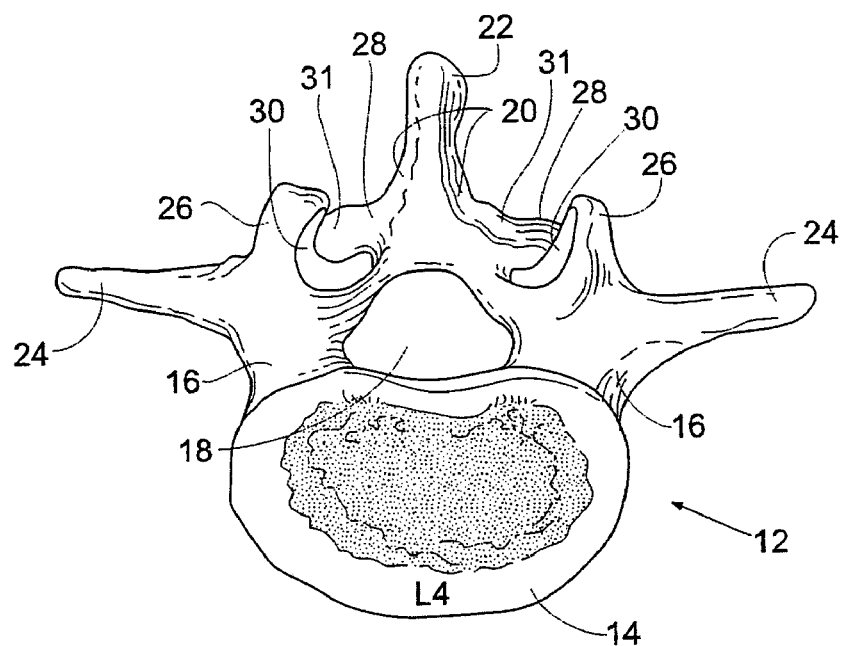
FIG. 2 is a superior view of a normal human lumbar vertebra.
Figure 3:
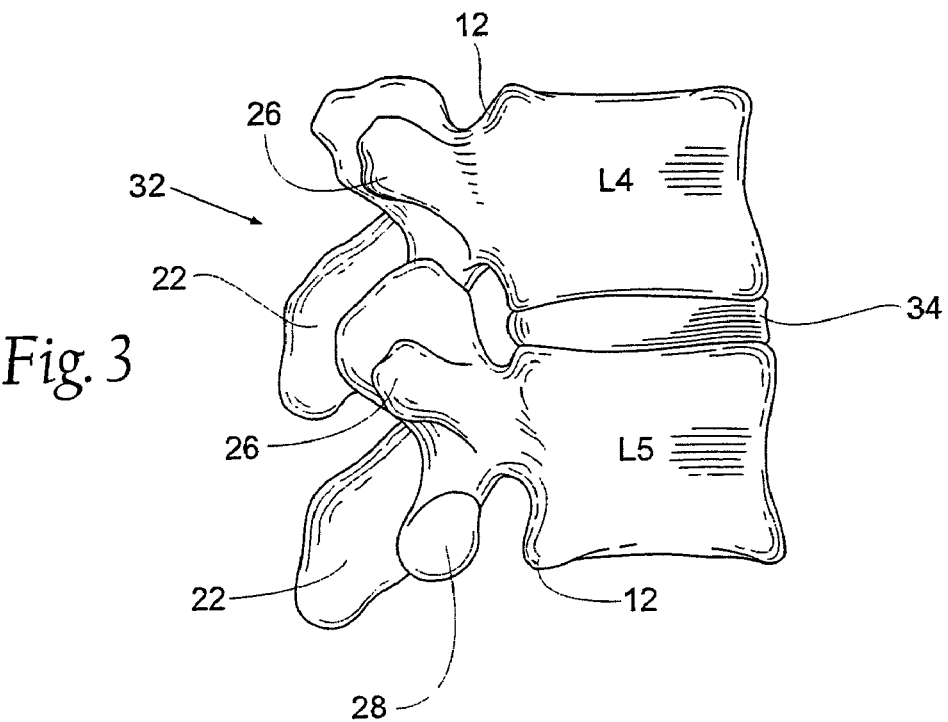
FIG. 3 is a lateral elevation view of a vertebral lumbar facet joint.
Figure 4:
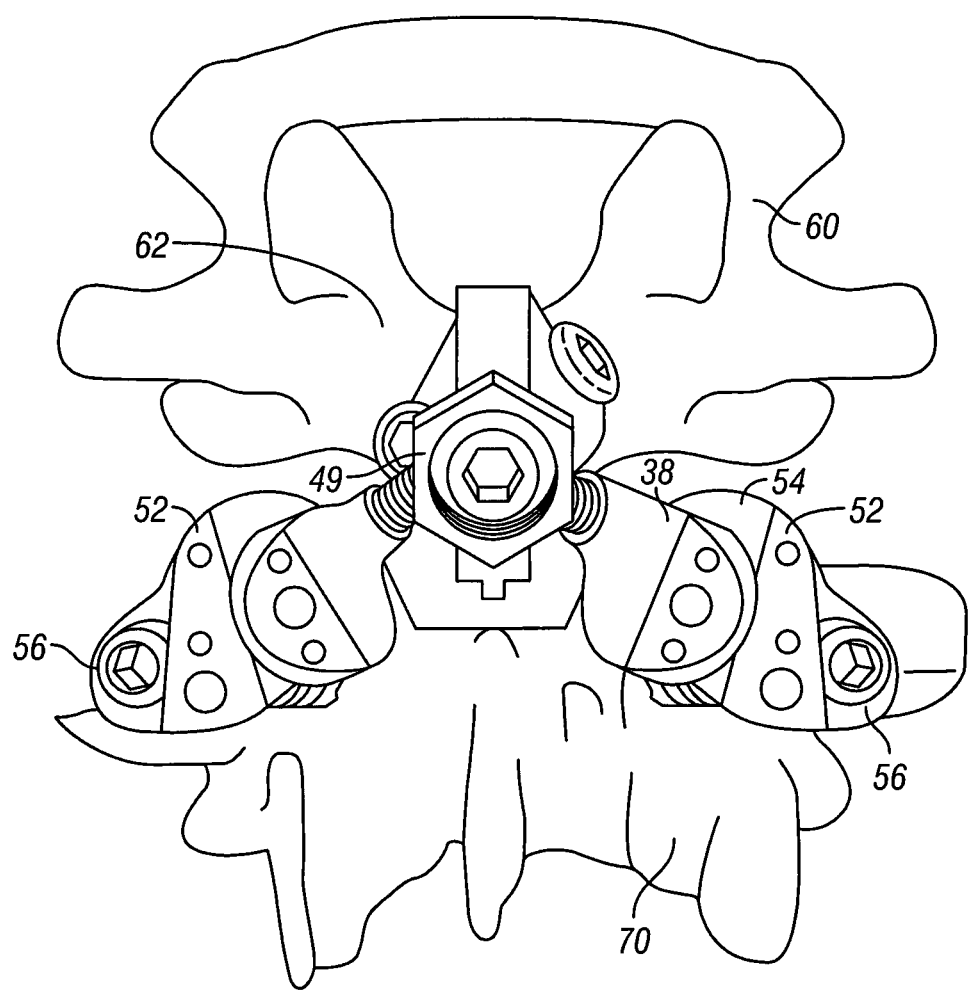
FIG. 4 is a posterior view of an artificial facet joint prosthesis installed in a patient according to one embodiment of this invention.
Figure 5:
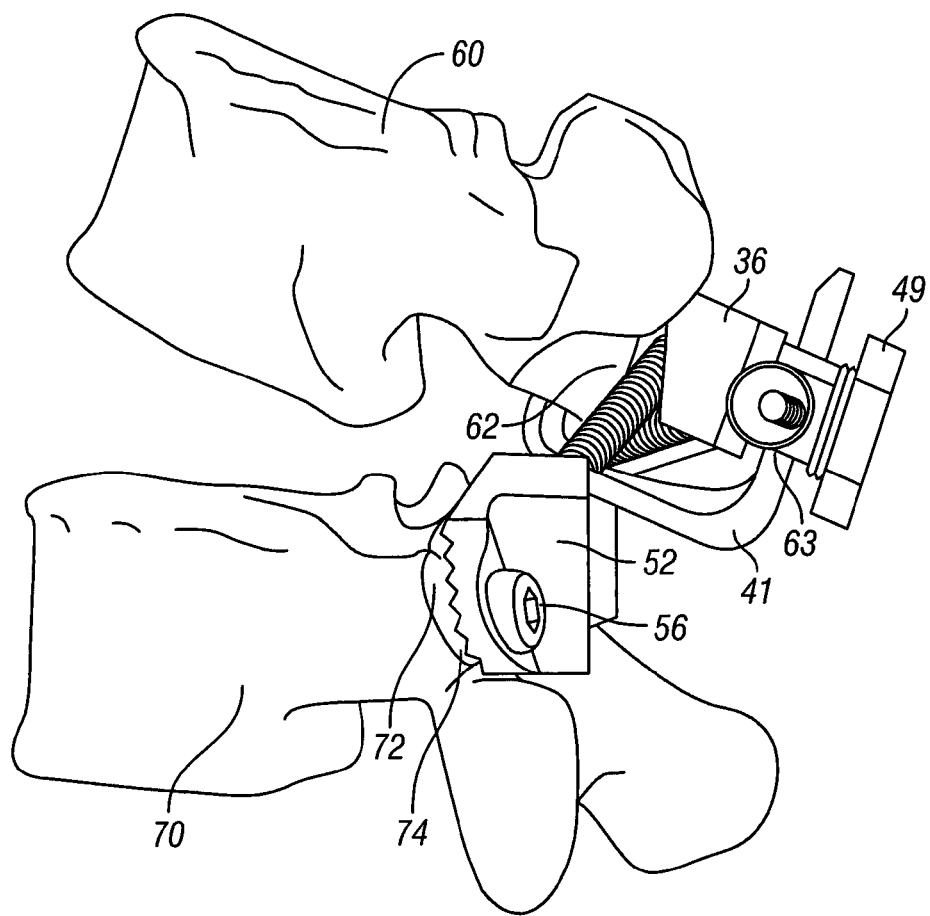
FIG. 5 is a left side view of the embodiment of FIG. 4, as installed in a patient.
Figure 6:
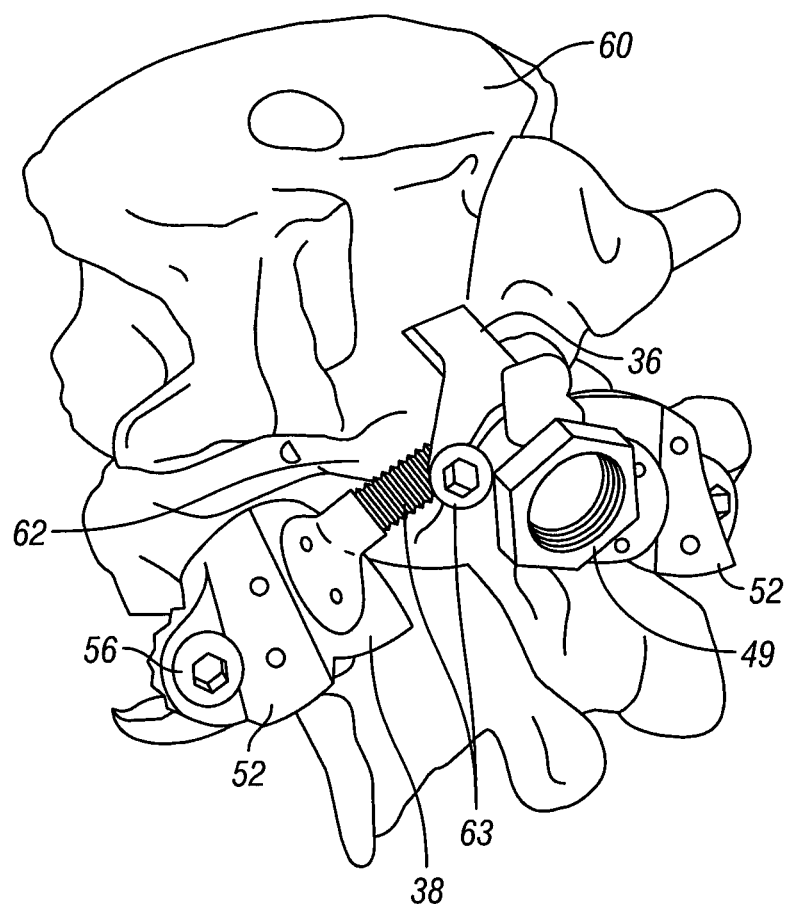
FIG. 6 is yet another view of the embodiment of FIG. 4, as installed in a patient.
Figure 7:
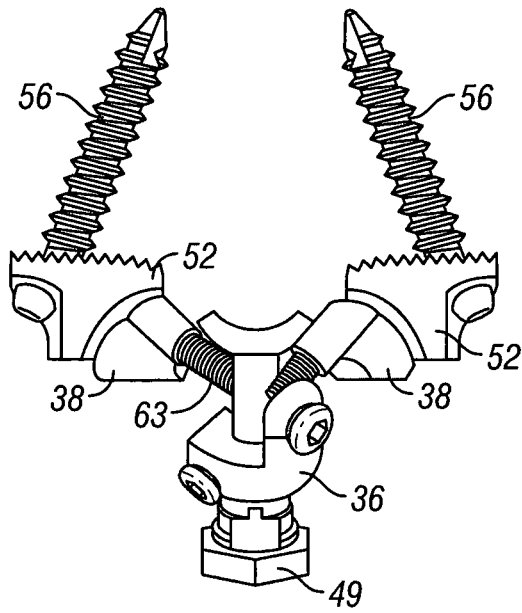
FIG. 7 is a top view of the artificial facet joint prosthesis of the embodiment of FIG. 4.
Figure 8:
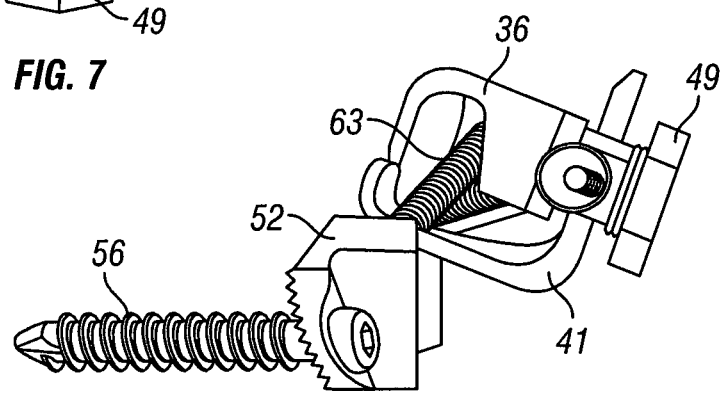
FIG. 8 is a left view of the artificial facet joint prosthesis of the embodiment of FIG. 4.
Figure 9:
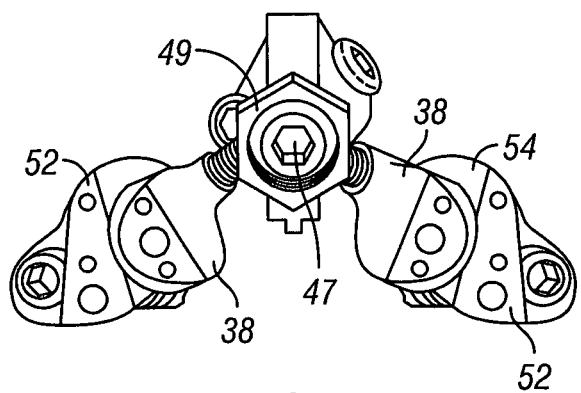
FIG. 9 is a posterior view of the artificial facet joint prosthesis of the embodiment of FIG. 4.
Figure 10:
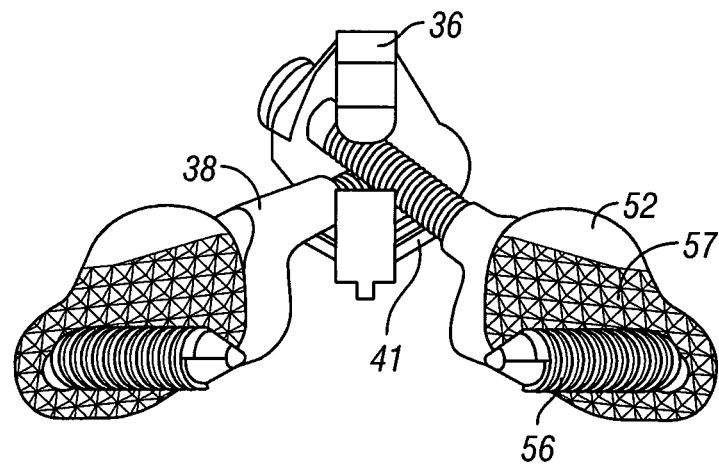
FIG. 10 is an anterior view of the artificial facet joint prosthesis of the embodiment of FIG. 4.
Figure 11:
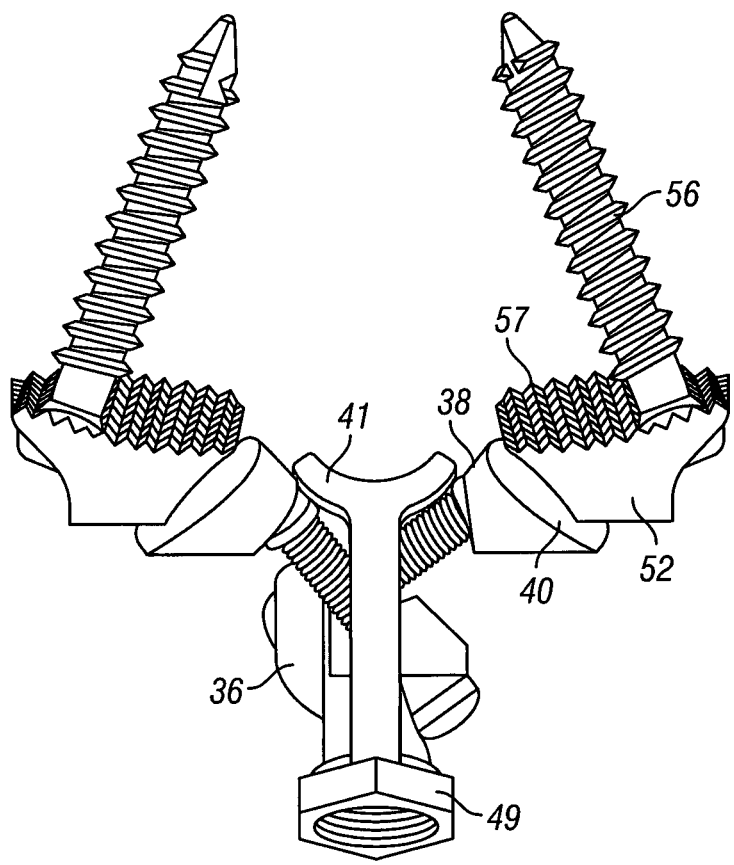
FIG. 11 is a bottom view of the artificial facet joint prosthesis of the embodiment of FIG. 4.

Depending on the patient's disease state, the condition of the patient's natural facet joint—including the facet joint's strength, location and orientation—may not be acceptable. As shown in FIGS. 4 and 5, therefore, the natural cephalad and caudal facet joint surfaces and the spinous process of vertebra 60 have been removed to enable the installation of a prosthetic facet joint without limitations presented by remaining portions of the natural facet joint. Other portions of the vertebra may be removed as required by the pathology of the patient's vertebrate).

A fixation mechanism attaches the cephalad prosthesis to vertebra 60. In this embodiment of the invention, the fixation mechanism includes a non-invasive support member such as a two-part clamp formed from an upper clamp member 36 and a lower clamp member 41. Upper clamp member 36 has a hook with a cephalad directed portion 51, an anteriorly directed portion 37 and a caudad directed portion 39. The anterior surface of cephalad directed portion 51, the bottom surface of anteriorly directed portion 37 and the posterior surface of caudad directed portion 39 are in contact with a contact portion of the patient's vertebra, shown as lamina portion 62 in FIGS. 4 and 5. Likewise, lower clamp member 41 has an anteriorly directed portion 42 and a cephalad directed portion 43. The top surface of anteriorly directed portion 42 and the posterior surface of cephalad directed portion 43 are also in contact with the contact portion of the vertebra, such as lamina portion 62 in FIGS. 4 and 5.

In this embodiment, the fixation mechanism of the cephalad prosthesis attaches to the lamina of vertebra 60 after removal of the spinous process from that vertebra. In other embodiments, the fixation mechanism may come in contact with other parts of the vertebra and at fewer than four contact points, such as by contacting two opposing sides of the vertebral contact portion. In addition, in other embodiments it may not be necessary to first remove the spinous process.

Figure 12:
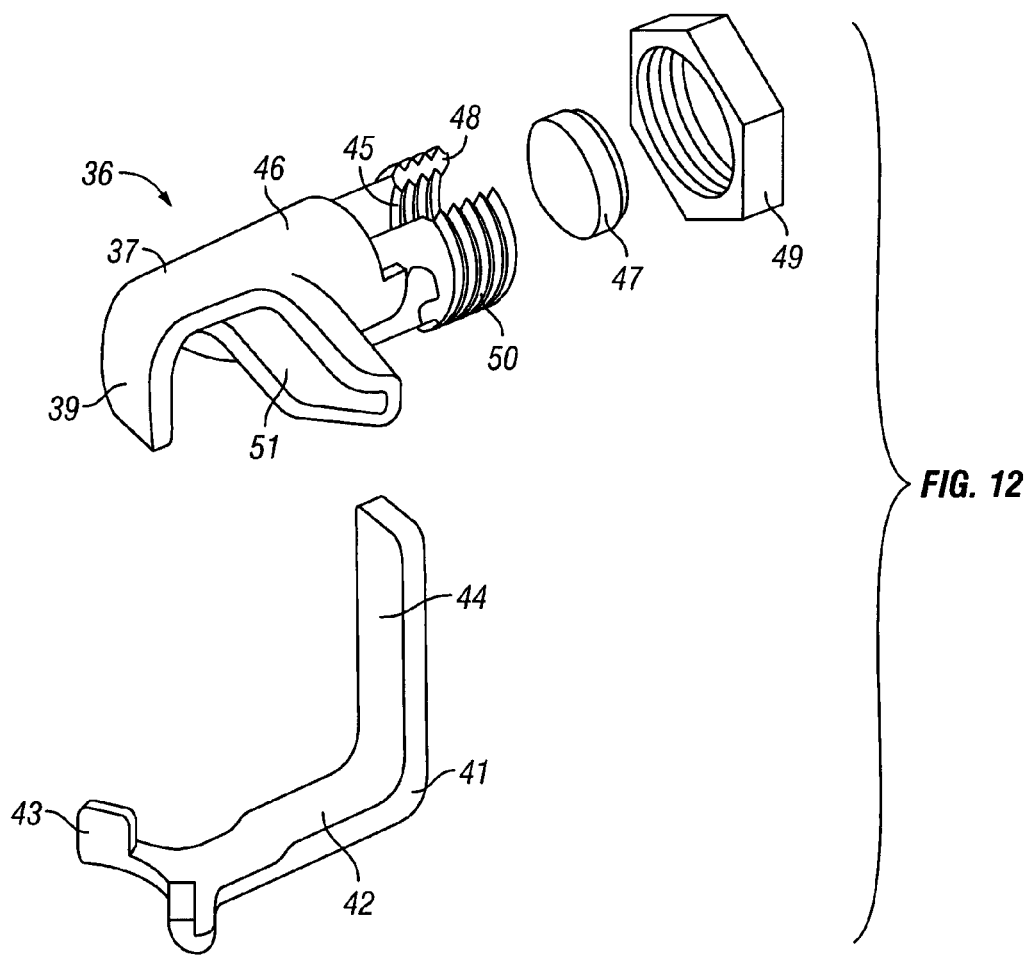
FIG. 12 is an exploded view of part of the cephalad portion of the artificial facet joint prosthesis of the embodiment of FIG. 4.
Figure 13:
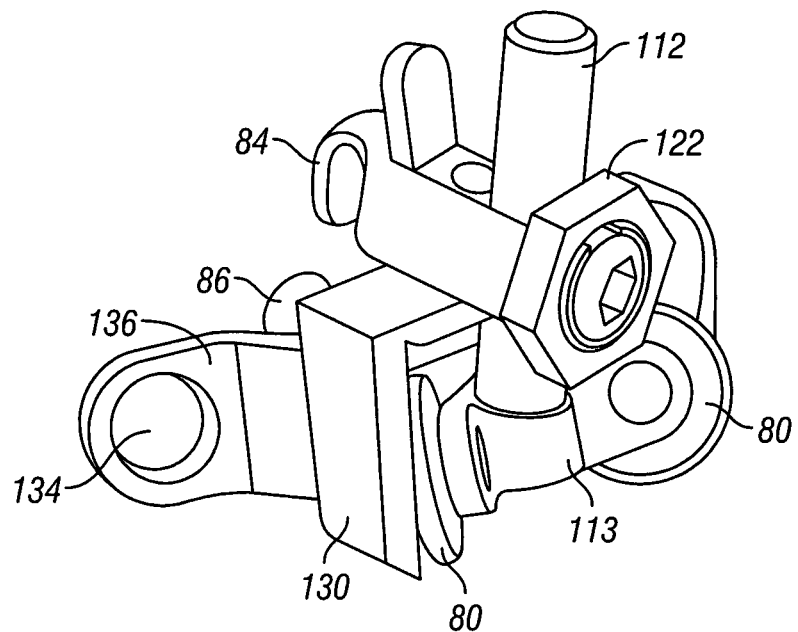
FIG. 13 is an artificial facet joint prosthesis according to another embodiment of this invention.
Figure 14:
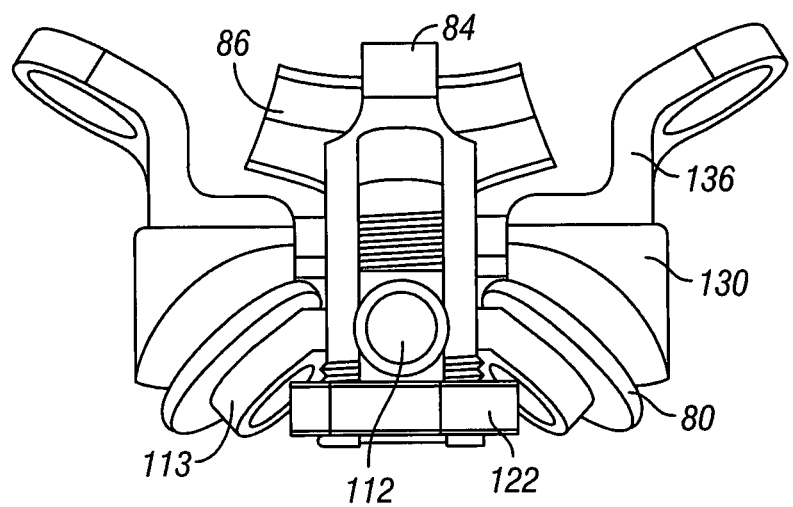
FIG. 14 is a top view of the artificial facet joint prosthesis of the embodiment of FIG. 13.
Figure 15:
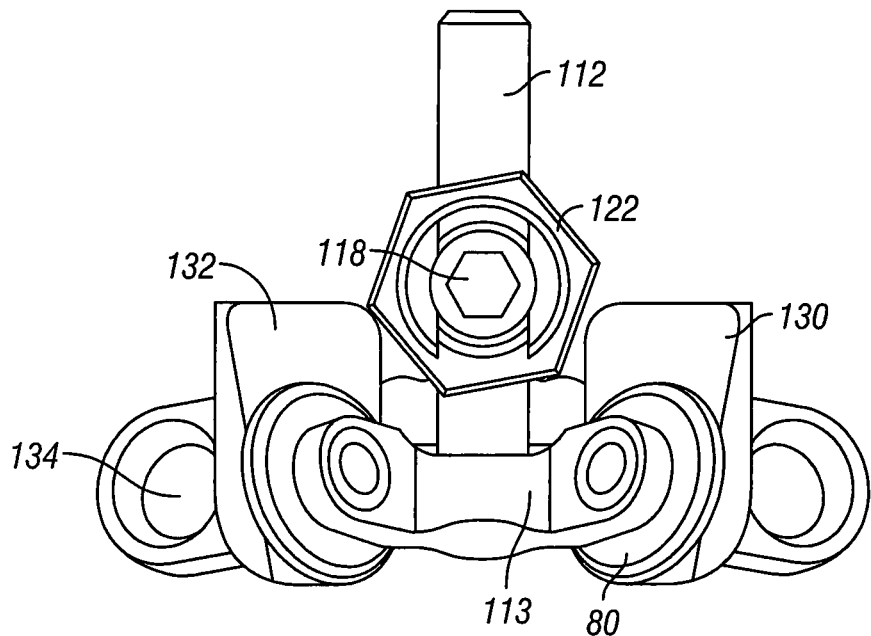
FIG. 15 is a posterior view of the artificial facet joint prosthesis of the embodiment of FIG. 13.
Figure 16:
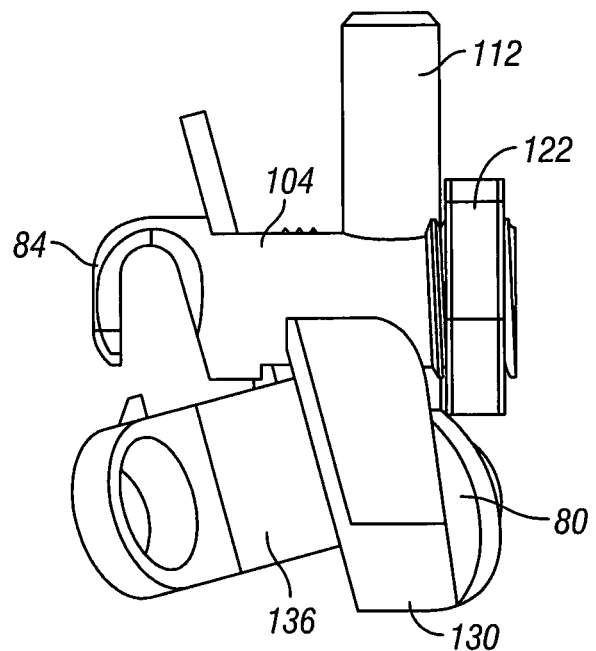
FIG. 16 is a left side view of the artificial facet joint prosthesis of the embodiment of FIG. 13.
Figure 17:
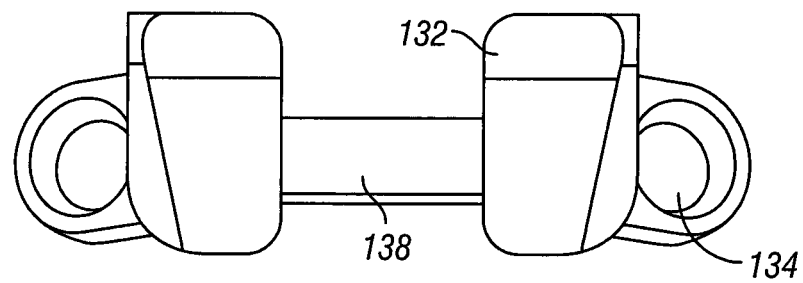
FIG. 17 is a posterior view of the caudal portion of the artificial facet joint prosthesis of the embodiment of FIG. 13.
Figure 18:
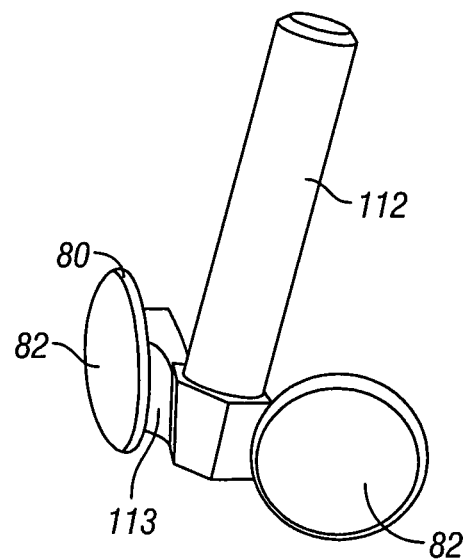
FIG. 18 is a view of the cephalad bearing elements of the artificial facet joint prosthesis of the embodiment of FIG. 13.

For purposes of installation and to conform most closely with the patient's anatomy, upper and lower clamp members 36 and 41 are movable with respect to each other. As shown in FIG. 12, a posterior cephalad directed portion 44 of clamp member 41 slides in a slot 45 formed posterior to a body portion 46 of upper clamp member 36. After placing upper clamp member 36 on contact portion 62 of vertebra 60, lower clamp member 41 may be slid upwards until it makes firm contact with contact portion 62 as well. A set screw 47 may be advanced within interior threads 48 formed in the posterior portion of upper clamp member 36 to firmly contact lower clamp member 41 to hold it in place. A nut 49 is then advanced onto exterior threads 50 formed in the posterior portion of upper clamp member 36 to lock set screw 47 and lower clamp member 41 in place.

The cephalad facet joint bearing elements 38 are attached to the assembly via an attachment mechanism. In the embodiment of FIGS. 4-12, the attachment mechanism includes fasteners such as screws 63 inserted through the body portion 46 of upper clamp member 36 into a hole formed in each bearing element 38. The angle in which screws 63 are inserted (and, therefore the relative orientation of the cephalad and caudal facet joint bearing elements) may be determined using tools such as those described in copending U.S. patent application Ser. No. 10/438,294 entitled "Prostheses, Tools and Methods for Replacement of Natural Facet Joints With Artificial Facet Joint Surfaces," filed May 14, 2003, the disclosure of which is incorporated herein by reference. As shown in FIGS. 4 and 5, if enough bone around the lamina portion of vertebra 60 is left intact, screws 63 may penetrate the lamina to form an additional fixation mechanism.

In an alternative embodiment, because of the amount of bone removed from the patient's vertebra prior to installation of the prosthesis, the attachment mechanism does not penetrate the bone. In this embodiment, the fasteners such as screws 63 are inserted through the body portion 46 of upper clamp member 36 into a threaded hole formed in each bearing element 38 but do not extend through the lamina or any other portion of the vertebra. As in the other embodiment, screws 63 traverse the midline of vertebra 60 and extend caudad from the clamp to provide the bearing element orientation shown. Other orientations of attachment mechanisms are possible, of course. In addition, the location of bearing elements 38 (i.e., in cephalad/caudad directions, left/right, etc.) may be adjusted by using different size or shape fasteners.

The artificial cephalad facet joint prosthesis of FIGS. 4-12 may be used with any suitable natural or artificial caudal facet joint members. FIGS. 4-12 show one suitable artificial caudal facet joint prosthesis that may be used. The caudal prosthesis has a bearing element 52 with a bearing surface 54. In this embodiment, bearing surface 54 is concave. Bearing element 52 may be formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts, and bearing surface 54 may be formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts.

In one embodiment, the natural caudal facet surface has been removed, and fixation element 56 attaches the caudal prosthesis to a vertebra 70 via a pedicle in an orientation and position that places bearing surface 54 in approximately the same location as the natural facet joint surface the prosthesis replaces. In an alternative embodiment, the bearing surface 54 may be placed in a location different than the natural facet joint surface, either more medial or more lateral, more cephalad or more caudad, and/or rotated from the natural anatomical orientation and orientation. In addition, in other embodiments the caudal component can be attached to the vertebral body in addition to the pedicle or to the vertebral body alone.

As shown in the embodiment of FIGS. 4-12, fixation element 56 is a screw attached to bearing element 54 via a hole formed in bearing element 52 and is inserted into a pedicle portion 72 of vertebra 70. Other possible fixation elements include stems, corkscrews, wire, staples, adhesives, bone cements, and other materials known in the prosthetic arts. Fixation element 56 can also be inserted into the vertebral body in addition to or in place of the pedicle.

In this embodiment, bearing element 52 has a serrated fixation surface 57 adapted to contact a contact portion 74 of vertebra 70. This optional fixation surface 57 helps prevent rotation of the bearing element 52. In addition, fixation surface 57 may be coated with bone ingrowth material, and any optional serrations increase the surface area for bone ingrowth. Further details regarding the design and installation of this caudal prosthesis may be found in copending and commonly owned U.S. patent application Ser. No. 10/438,294 entitled "Prostheses, Tools and Methods for Replacement of Natural Facet Joints With Artificial Facet Joint Surfaces," filed May 14, 2003.

FIGS. 13-20 show another embodiment of the artificial facet joint prosthesis of this invention for replacing a natural facet joint. The cephalad prosthesis has a bearing element 80 with a bearing surface 82. In this embodiment, bearing surface 82 has a convex shape. Bearing element 80 and bearing surface 82 may be formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts.

A fixation mechanism attaches the cephalad prosthesis to the vertebra. In this embodiment of the invention, the fixation mechanism includes a non-invasive support member such as a two-part clamp formed from an upper clamp member 84 and a lower clamp member 86. Upper clamp member 84 has a hook with a cephalad directed portion 88, an anteriorly directed portion 90 and a caudad directed portion 92. The anterior surface of cephalad directed portion 88, the bottom surface of anteriorly directed portion 90 and the posterior surface of caudad directed portion 92 are in contact with a contact portion of the patient's vertebra (such as the lamina) when the prosthesis is installed in a patient. Likewise, lower clamp member 86 has a caudad directed portion 94, an anteriorly directed portion 96 and a cephalad directed portion 98. The anterior surface of caudad directed portion 94, the top surface of anteriorly directed portion 96 and the posterior surface of cephalad directed portion 98 are also in contact with the contact portion of the vertebra (such as the lamina) when the prosthesis is installed in a patient. This arrangement of upper and lower clamps provides for contact with the lamina (or other vertebra contact portion) on four sides.

In this embodiment, the fixation mechanism of the cephalad prosthesis attaches to the lamina of vertebra after removal of the spinous process from that vertebra. In other embodiments, the fixation mechanism may come in contact with other parts of the vertebra and at fewer than four contact points, such as by contacting two opposing sides of the vertebral contact portion. In addition, in other embodiments it may not be necessary to first remove the spinous process.

Figure 19:
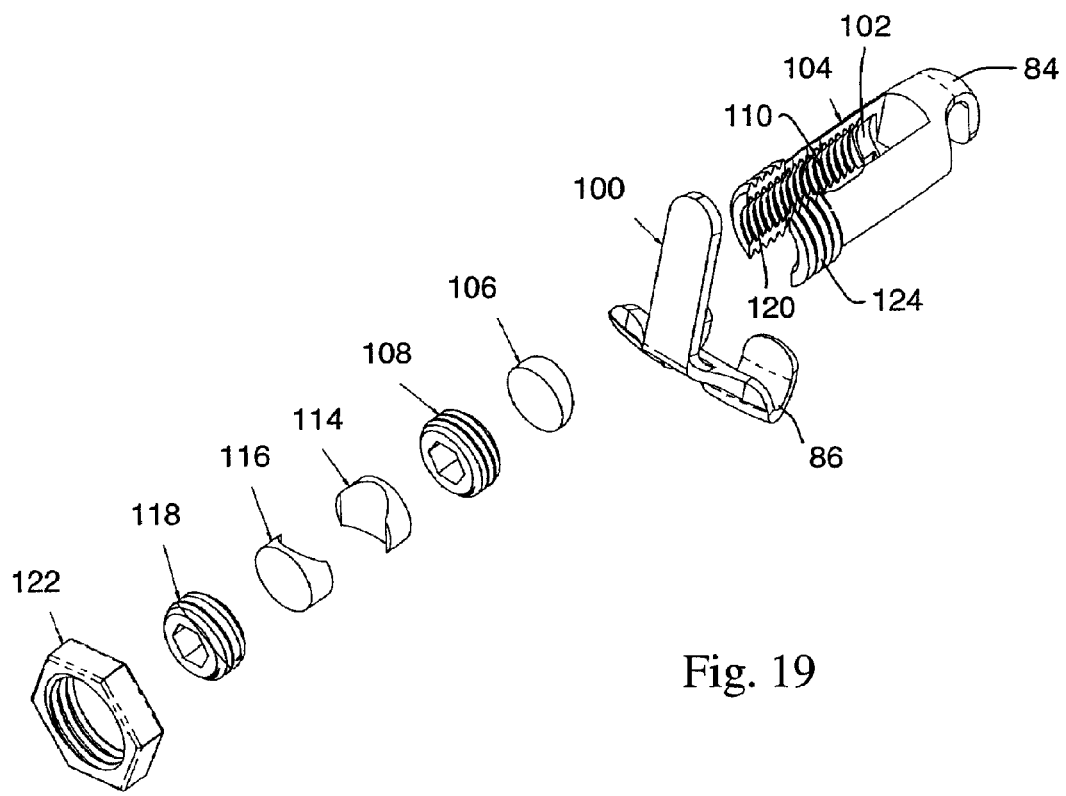
FIG. 19 is an exploded view of a clamp assembly according to the embodiment of FIG. 13.
Figure 20:
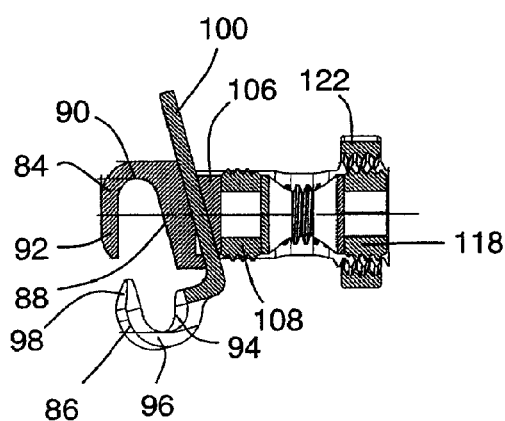
FIG. 20 is a cross-sectional view of the clamp assembly of FIG. 19.

For purposes of installation and to conform most closely with the patient's anatomy, upper and lower clamp members 84 and 86 are movable with respect to each other. As shown in FIGS. 19 and 20, a posterior cephalad directed portion 100 of clamp member 86 slides in a slot 102 formed in a body portion 104 of upper clamp member 84. As shown, slot 102 places clamp member portion 100 at a 15° angle from vertical, and a shim 106 is placed posterior to clamp member portion 100. This orientation may be changed, of course, to meet the needs of the patient's anatomy.

After placing upper clamp member 84 on the contact portion of the vertebra, lower clamp member 86 may be slid upwards until it makes firm contact with the contact portion as well. A set screw 108 is then advanced within interior threads 110 formed in body portion 104 of upper clamp member 84 to firmly contact lower clamp member 86 to hold it in place.

The cephalad facet joint bearing elements 80 are attached to the assembly via an attachment mechanism, including a movable location element for adjusting the location of bearing elements 80. In this embodiment, the location element includes a rod 112 to which bearing elements 80 are attached via attachment wings 113. During installation, rod 112 is movable in a space formed by a pair of inserts 114 and 116 to adjust the location of bearing elements 80. Once the location has been set, inserts 114 and 116 are tightened against rod 112 by advancing a second set screw 118 against insert 116 via internal threads 120 formed in the body portion of the upper clamp member. A nut 122 is then advanced onto exterior threads 124 formed in the body portion of upper clamp member 84 to the other components in place.

The artificial cephalad facet joint prosthesis of FIGS. 13-16 and 18-20 may be used with any suitable natural or artificial caudal facet joint members. FIGS. 13-17 show one suitable artificial caudal facet joint prosthesis that may be used. The caudal prosthesis has a bearing element 130 with a bearing surface 132. In this embodiment, bearing surface 132 is concave. Bearing element 130 and bearing surface 132 may be formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts.

To install the artificial caudal prosthesis of this embodiment, the natural caudal facet surface is removed, and a fixation element (such as a screw) is inserted through holes 134 formed in arms 136 extending from bearing elements 130 into pedicle portions of a vertebra to attach the caudal prosthesis to the vertebra in an orientation and position that places bearing surface 132 in approximately the same location as the natural facet joint surface the prosthesis replaces. The spacing between bearing elements 130 is set by a bar 138. In an alternative embodiment, the bearing surface may be placed in a location different than the natural facet joint surface, either more medial or more lateral, more cephalad or more caudad, and/or rotated from the natural anatomical orientation. In addition, in other embodiments the caudal component can be attached to the vertebral body in addition to the pedicle or to the vertebral body alone. Other possible fixation elements include stems, corkscrews, wire, staples, adhesives, bone cements, and other materials known in the prosthetic arts.

As shown in the preceding embodiments of the invention, unlike other facet joint prostheses that attach to the pedicle, the use of one or more posterior elements of the vertebra to attach the cephalad facet joint prosthesis of this invention does not block access to the pedicle area, leaving this area free to be used to attach other prostheses or devices. Other embodiments of the invention may block the pedicle area, of course, without departing from the scope or spirit of the invention. Also, in some embodiments, the entire prosthesis other than the bearing surface may be coated with bone ingrowth material.

The above described embodiments of this invention are merely descriptive of its principles and are not to be limited. The scope of this invention instead shall be determined from the scope of the following claims, including their equivalents.

What is claimed is:

1. A facet replacement device adapted to engage a laminar surface on a first spinal vertebra and a second laminar surface on a second spinal vertebra, the device comprising:
   an upper clamp adapted to attach to the laminar surface on the first spinal vertebra; and
   a lower clamp, adapted to engage the upper clamp, adapted to attach to the laminar surface on the second spinal vertebra,
   wherein the upper clamp is configured with a slot for receiving a portion of the lower clamp thereby enabling the lower clamp to slide within the slot of the upper clamp, wherein the upper clamp articulates with respect to the lower clamp, wherein the upper clamp is separate from the lower clamp, wherein the upper clamp includes a first contact surface adapted to contact the first spinal vertebra and the lower clamp includes a second contact surface adapted to contact the second spinal vertebra.

2. The facet replacement device of claim 1 wherein the device is further adapted to provide a hook on at least one of the upper clamp or the lower clamp.

3. The facet replacement device of claim 1 wherein the device is further adapted to provide an upper clamp bearing surface in communication with a lower clamp bearing surface.

4. The facet replacement device of claim 3 wherein the upper clamp bearing surface and lower clamp bearing surface are adapted to provide a flexible material therebetween.

5. The facet replacement device of claim 1 wherein the upper clamp and the lower clamp are adapted to provide an aperture for mounting the upper clamp and the lower clamp to one of the first spinal vertebra and the second spinal vertebra with the use of a fastener.

6. A facet replacement device adapted to engage a first surface on a first spinal vertebra and a second surface on a second spinal vertebra, the device comprising:
an upper clamp adapted to attach to the first surface on the first spinal vertebra;
a lower clamp, adapted to engage the upper clamp, adapted to attach to the second surface on the second spinal vertebra; and
a flexible material positioned between the upper clamp and the lower clamp,
wherein the upper clamp is configured with a slot for receiving a portion of the lower clamp thereby enabling the lower clamp to slide within the slot of the upper clamp,
wherein the upper clamp articulates with respect to the lower clamp,
wherein the upper clamp is separate from the lower clamp, wherein the upper clamp includes a first contact surface adapted to contact the first spinal vertebra and the lower clamp includes a second contact surface adapted to contact the second spinal vertebra.

7. The facet replacement device according to claim 6 wherein the upper clamp is adapted to provide a hook for engaging a portion of the spinal vertebra.

8. The facet replacement device according to claim 6 wherein the lower clamp is adapted to provide a hook for engaging a portion of the spinal vertebra.

9. The facet replacement device of claim 6 wherein the device is further adapted to provide an upper clamp bearing surface in communication with a lower clamp bearing surface.

10. The facet replacement device of claim 6 wherein the upper clamp and the lower clamp are adapted to provide an aperture for mounting the upper clamp and the lower clamp to one of the first spinal vertebra and the second spinal vertebra with the use of a fastener.

11. A facet replacement device adapted to engage a first surface on a first spinal vertebra and a second surface on a second spinal vertebra, the device comprising:
an upper clamp adapted to attach to the first surface on the first spinal vertebra;
a lower clamp, adapted to engage the upper clamp, adapted to attach to the second surface on the second spinal vertebra; and wherein the upper clamp is adapted to provide a hook for engaging a portion of the spinal vertebra,
wherein the upper clamp is configured with a slot for receiving a portion of the lower clamp thereby enabling the lower clamp to slide within the slot of the upper clamp, and
wherein the upper clamp articulates with respect to the lower clamp,
wherein the upper clamp is separate from the lower clamp, wherein the upper clamp includes a first contact surface adapted to contact the first spinal vertebra and the lower clamp includes a second contact surface adapted to contact the second spinal vertebra.

12. The facet replacement device according to claim 11 wherein the lower clamp is adapted to provide a hook for engaging a portion of the spinal vertebra.

13. The facet replacement device of claim 12 wherein the device is further adapted to provide an upper clamp bearing surface in communication with a lower clamp bearing surface.

14. The facet replacement device of claim 12 wherein the upper clamp and the lower clamp are adapted to provide an aperture for mounting the upper clamp and the lower clamp to one of the first spinal vertebra and the second spinal vertebra with the use of a fastener.

15. The facet replacement device of claim 12 wherein the upper clamp bearing surface and lower clamp bearing surface are adapted to provide a flexible material therebetween.

16. A method for restoring range of motion between vertebral bodies of a spine comprising the steps of:
implanting a facet replacement device adapted to engage a first surface on a first spinal vertebra and a second surface on a second spinal vertebra, the device comprising:
an upper clamp adapted to attach to the first surface on the first spinal vertebra;
a lower clamp, adapted to engage the upper clamp, adapted to attach to the second surface on the second spinal vertebra; and
a flexible material positioned between the upper clamp and the lower clamp
wherein the upper clamp is configured with a slot for receiving a portion of the lower clamp thereby enabling the lower clamp to slide within the slot of the upper clamp,
wherein the upper clamp articulates with respect to the lower clamp,
wherein the upper clamp is separate from the lower clamp, wherein the upper clamp includes a first contact surface that contacts the first spinal vertebra and the lower clamp includes a second contact surface that contacts the second spinal vertebra.

17. The method for restoring range of motion between vertebral bodies of a spine according to claim 16 further comprising the step of engaging the first spinal vertebra by hooking a portion of the upper clamp to the spinal vertebra.

18. The method for restoring range of motion between vertebral bodies of a spine according to claim 16 further comprising the step of engaging the second spinal vertebra by hooking a portion of the lower clamp to the spinal vertebra.

19. The method for restoring range of motion between vertebral bodies of a spine according to claim 17 further comprising the step of engaging the upper clamp to the first spinal vertebra by use of a fastener.

20. The method for restoring range of motion between vertebral bodies of a spine according to claim 17 further comprising the step of engaging the upper clamp to the first spinal vertebra by use of a fastener.

\* \* \* \* \*